United States Patent
Steller et al.

(10) Patent No.: US 10,596,390 B2
(45) Date of Patent: Mar. 24, 2020

(54) ADVANCED APPLICATOR SYSTEMS AND METHODS

(71) Applicant: NUCLETRON OPERATIONS B.V., Veenendaal (NL)

(72) Inventors: Hendrik Steller, Rhenen (NL); Wilhelmus Van Erp, Leek (NL); Jan Willem Van Manen, Veenendaal (NL); Norbert Johan Lukas Geheniau, Veenendaal (NL)

(73) Assignee: NUCLETRON OPERATIONS B.V., Veenendaal (NL)

( * ) Notice: Subject to any disclaimer, the term of this patent is extended or adjusted under 35 U.S.C. 154(b) by 156 days.

(21) Appl. No.: 15/532,050

(22) PCT Filed: Dec. 4, 2015

(86) PCT No.: PCT/IB2015/002480
§ 371 (c)(1),
(2) Date: May 31, 2017

(87) PCT Pub. No.: WO2016/087946
PCT Pub. Date: Jun. 9, 2016

(65) Prior Publication Data
US 2017/0291041 A1    Oct. 12, 2017

Related U.S. Application Data

(60) Provisional application No. 62/087,714, filed on Dec. 4, 2014, provisional application No. 62/242,658, filed on Oct. 16, 2015.

(51) Int. Cl.
*A61N 5/10* (2006.01)
*A61B 1/303* (2006.01)
*A61B 17/02* (2006.01)

(52) U.S. Cl.
CPC ......... *A61N 5/1016* (2013.01); *A61N 5/1007* (2013.01); *A61N 5/1027* (2013.01); *A61B 1/303* (2013.01); *A61B 17/0206* (2013.01)

(58) Field of Classification Search
CPC .................. A61N 5/1016; A61N 5/1001–1027
See application file for complete search history.

(56) References Cited

U.S. PATENT DOCUMENTS 4,554,909 A * 11/1985 Pino y Torres ...... A61N 5/1016
600/6
6,129,670 A    10/2000 Burdette et al.
(Continued)

FOREIGN PATENT DOCUMENTS

| CN | 101005875 A | 7/2007 |
| CN | 102378639 A | 3/2012 |

(Continued)

OTHER PUBLICATIONS

International Search Report and Written Opinion in PCT/IB2015/002480 dated May 17, 2016.
(Continued)

*Primary Examiner* — Thaddeus B Cox
(74) *Attorney, Agent, or Firm* — Finnegan, Henderson, Farabow, Garrett & Dunner LLP

(57) ABSTRACT

Systems, methods, and apparatuses are provided for an advanced gynecological applicator. In accordance with some embodiments, a brachytherapy applicator head and assembly is provided. The assembly may include two ovoid tubes configured to receive radiation sources, the two ovoid tubes combining to form a rounded applicator having a middle opening and comprising a plurality of needle holes to guide interstitial needles. The assembly may also include a central applicator tube configured to receive a radiation source that is located within the middle opening. Additionally, the assembly may include a vaginal cap that includes a tool-free (Continued)

connection to the two ovoid tubes and includes needle guides that align with the needle holes of the two ovoid tubes. The assembly may include a one-piece template for securing interstitial needles. The assembly may further include a tool-free connector to secure the two ovoid tubes to the central applicator tube.

21 Claims, 39 Drawing Sheets

(56) References Cited

U.S. PATENT DOCUMENTS

| | | | | |
|---|---|---|---|---|
| 6,312,375 | B1* | 11/2001 | Montebello | A61N 5/1016 600/3 |
| 2003/0084909 | A1 | 5/2003 | Burdette et al. | |
| 2008/0064916 | A1* | 3/2008 | Mick | A61N 5/1016 600/6 |
| 2012/0029263 | A1* | 2/2012 | Wardt | A61M 25/01 600/7 |
| 2013/0053682 | A1* | 2/2013 | Esthappan | A61N 5/10 600/411 |
| 2013/0317276 | A1* | 11/2013 | D'Andrea | A61N 5/1016 600/2 |

FOREIGN PATENT DOCUMENTS

| | | |
|---|---|---|
| EP | 1 854 507 A1 | 11/2007 |
| EP | 2 239 005 A1 | 10/2010 |
| JP | 2012-522545 | 9/2012 |
| RU | 2515527 | 5/2014 |
| WO | WO 2006/014701 A2 | 2/2006 |
| WO | WO 2007/149578 A2 | 12/2007 |
| WO | WO 2016/087946 A1 | 6/2016 |

OTHER PUBLICATIONS

Elekta: "Utrecht Interstitial applicator", May 28, 2014.

Kirisits C et al.: "The Vienna applicator for combined intracavitary and interstitial brachytherapy of cervical cancer: Design, application, treatment planning, and dosimetric results", *International Journal of Radiation: Oncology Biology Physics*, Pergamon Press, USA, vol. 65, No. 2, Jun. 1, 2006, pp. 624-630.

FIPS Search Report from corresponding Russian Application No. 2017123033 dated Feb. 18, 2019 (2 pages).

Office Action form corresponding Russian Application No. 2017123033 dated Feb. 18, 2019 (6 pages).

The First Office Action from the National Intellectual Property Administration of the People's Republic of China for corresponding Chinese Patent Application No. 201580075572.9 dated Mar. 13, 2019.

Australian Examination Report in corresponding Australian Application No. 2015356775 dated Jul. 31, 2019 in the Australian Government IP Office (6 pages).

Japanese Office Action dated Aug. 26, 2019, in corresponding application No. 2017-530029.

* cited by examiner

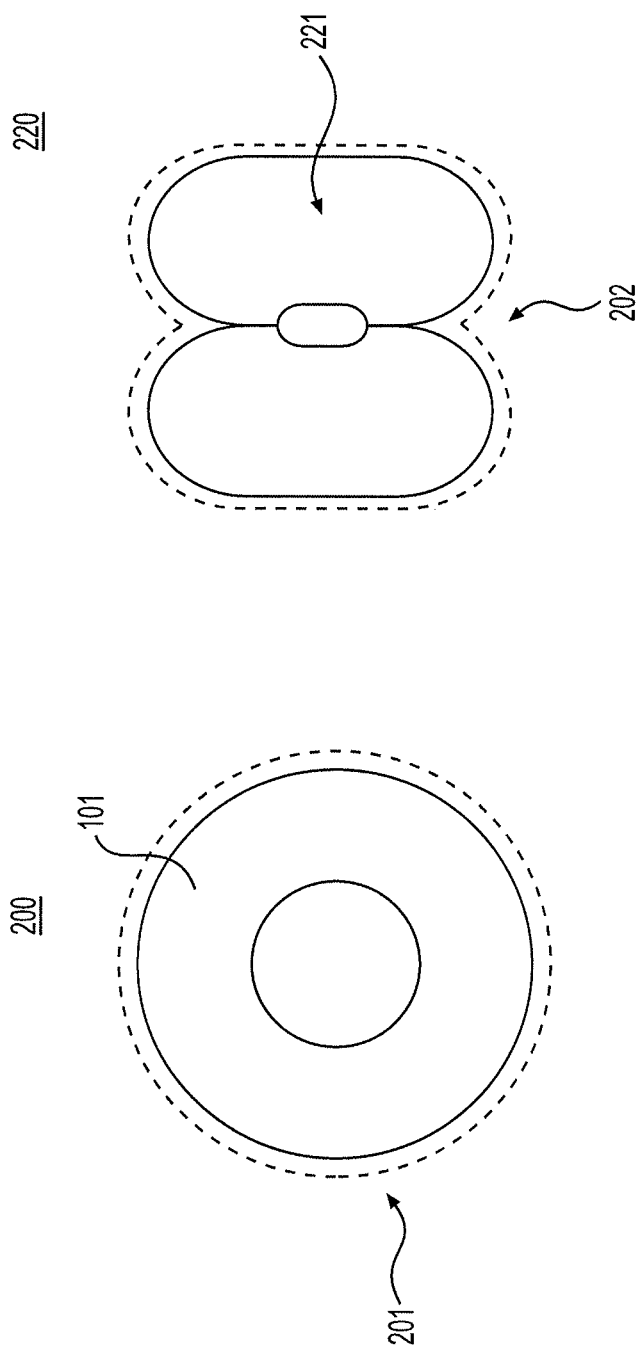

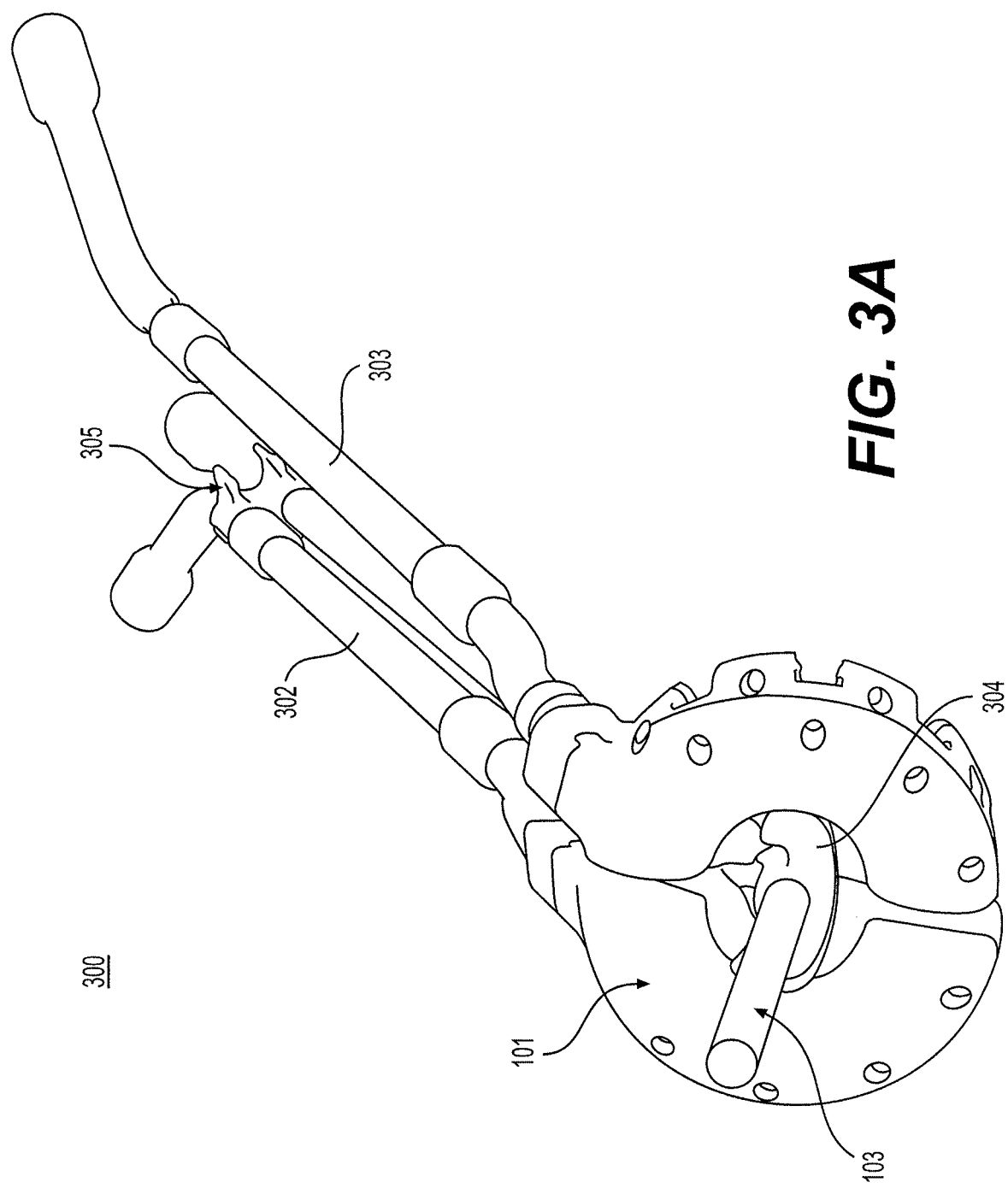

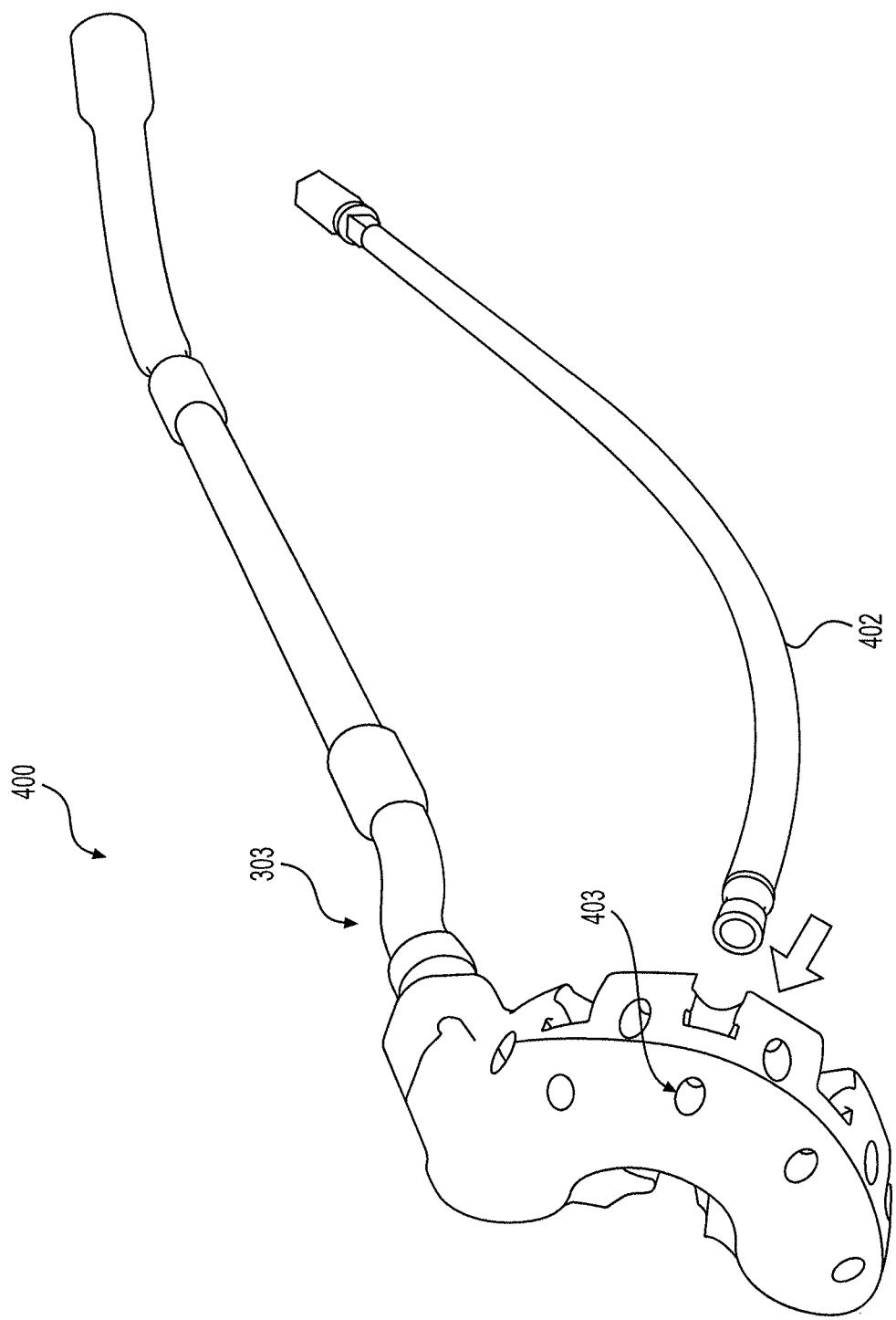

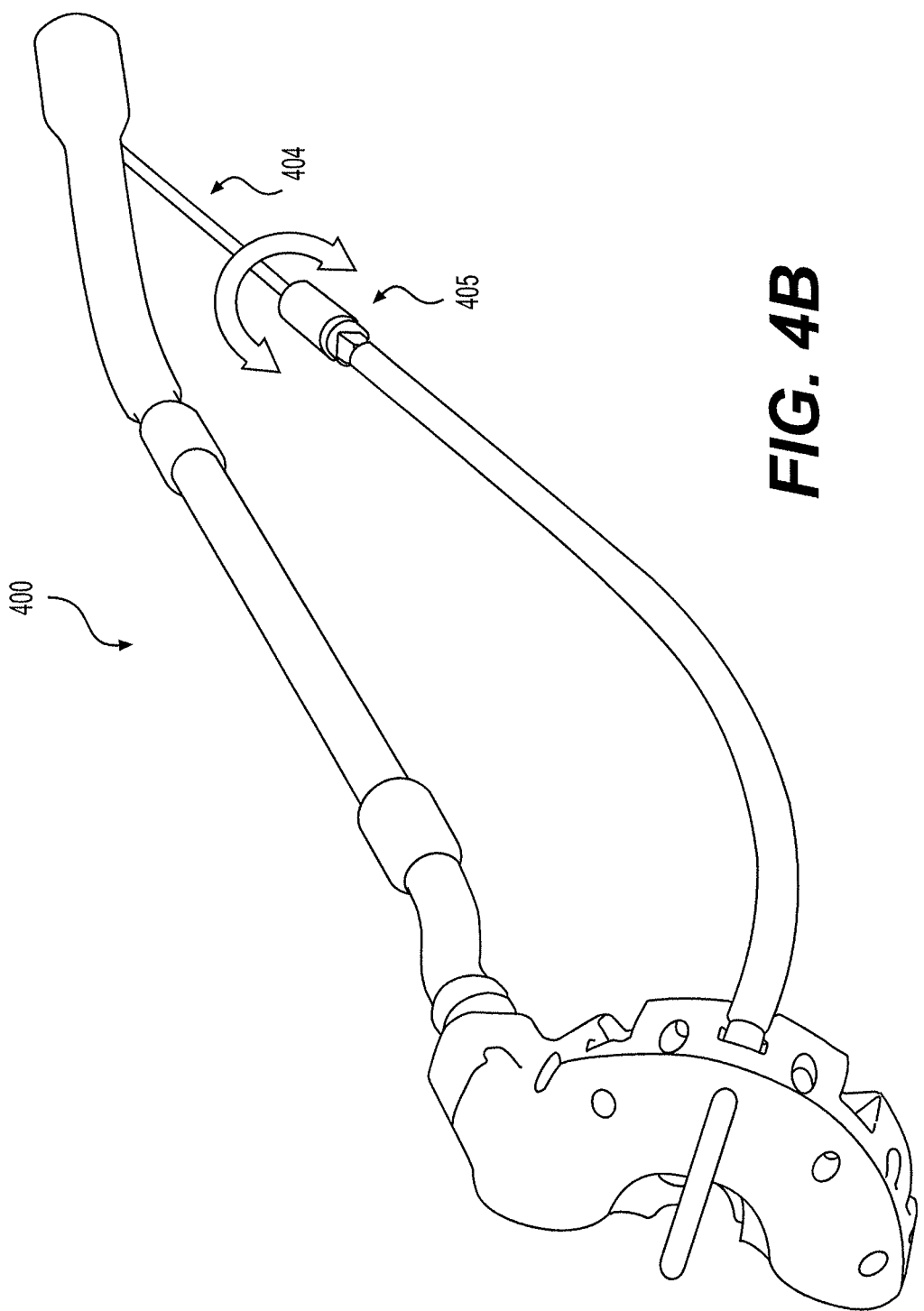

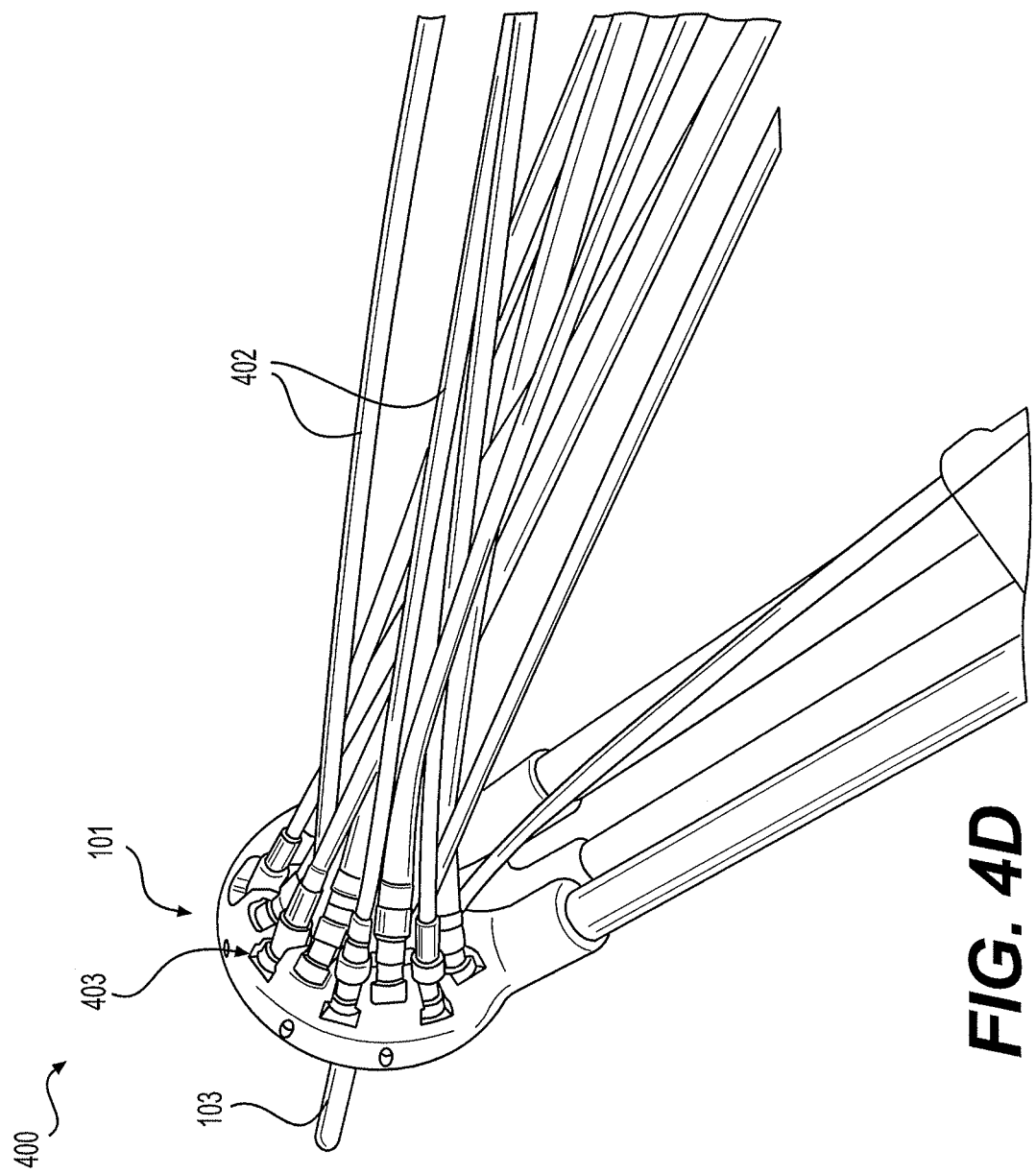

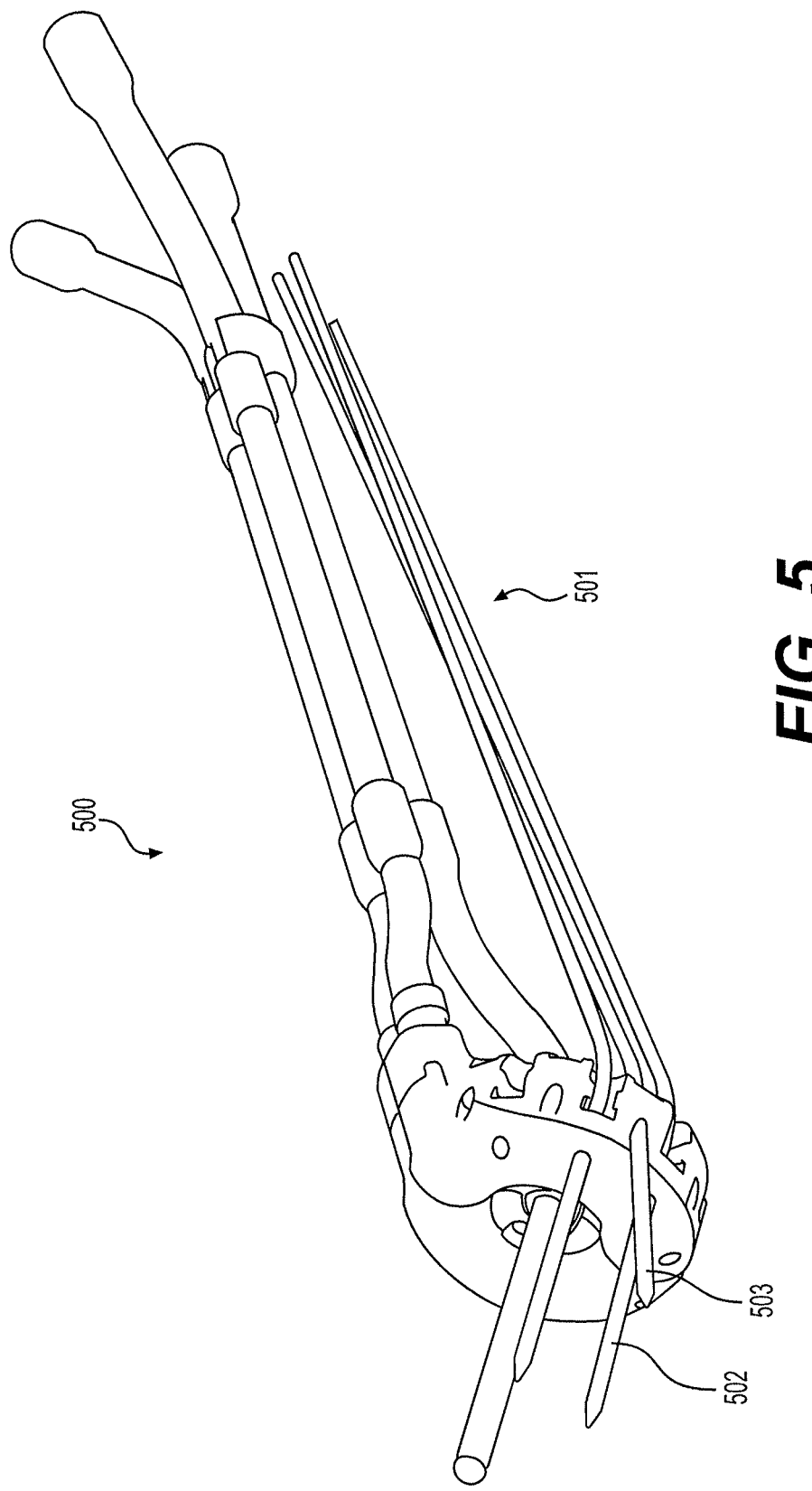

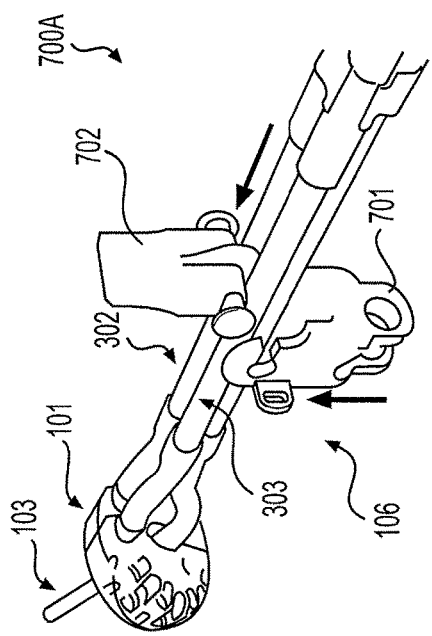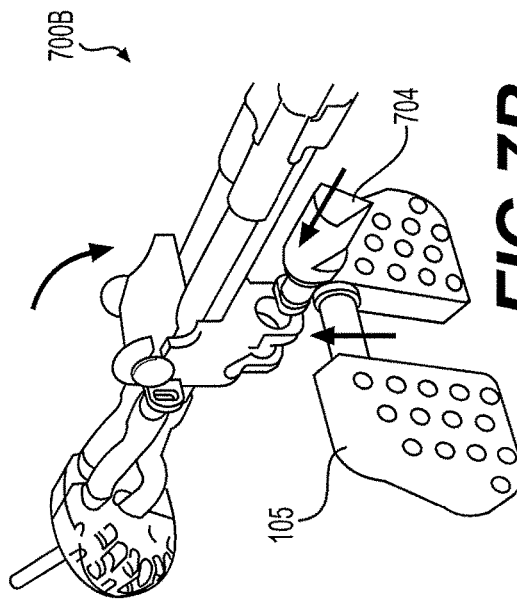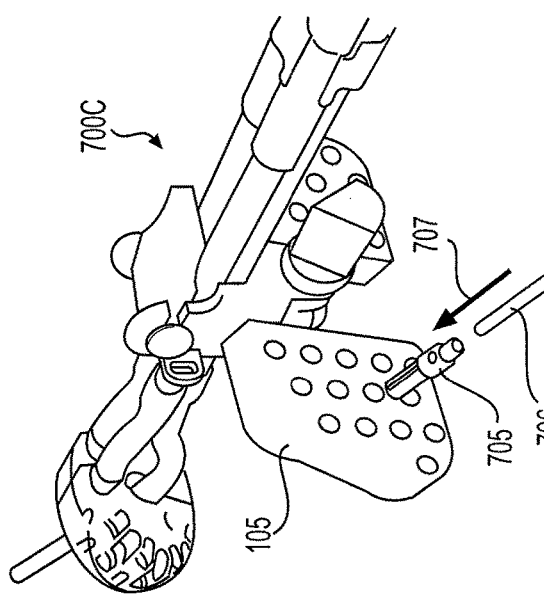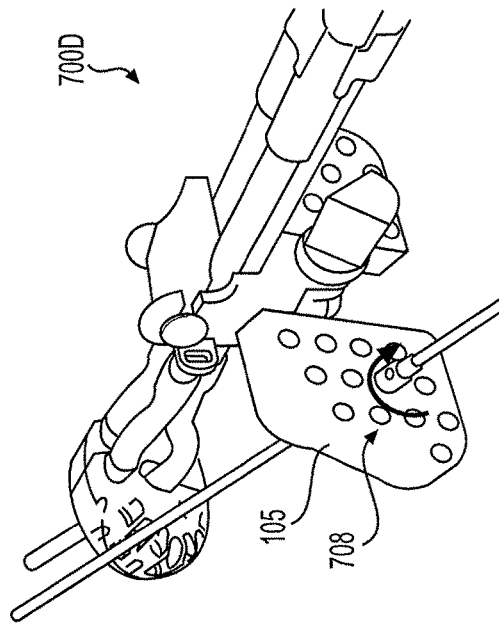

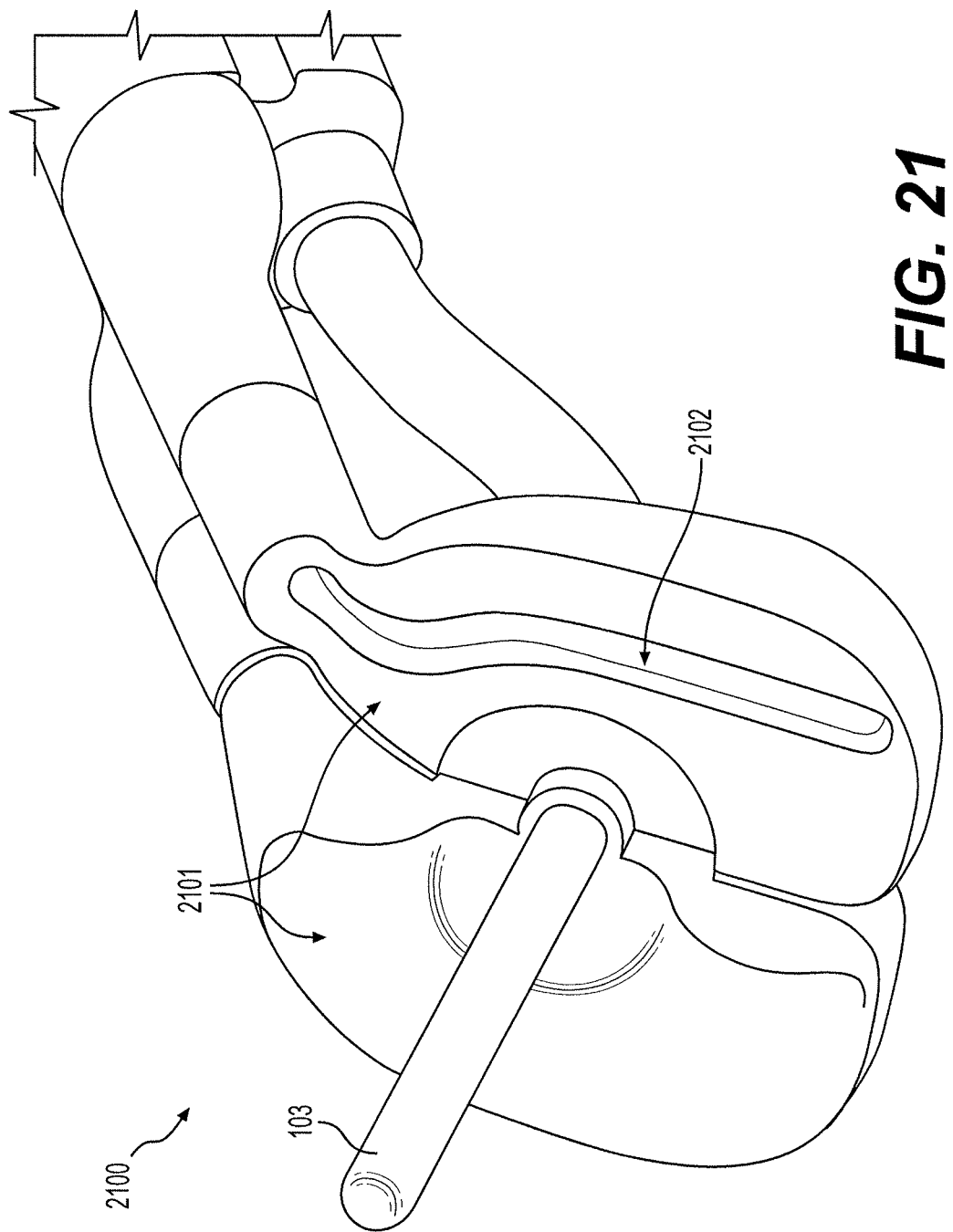

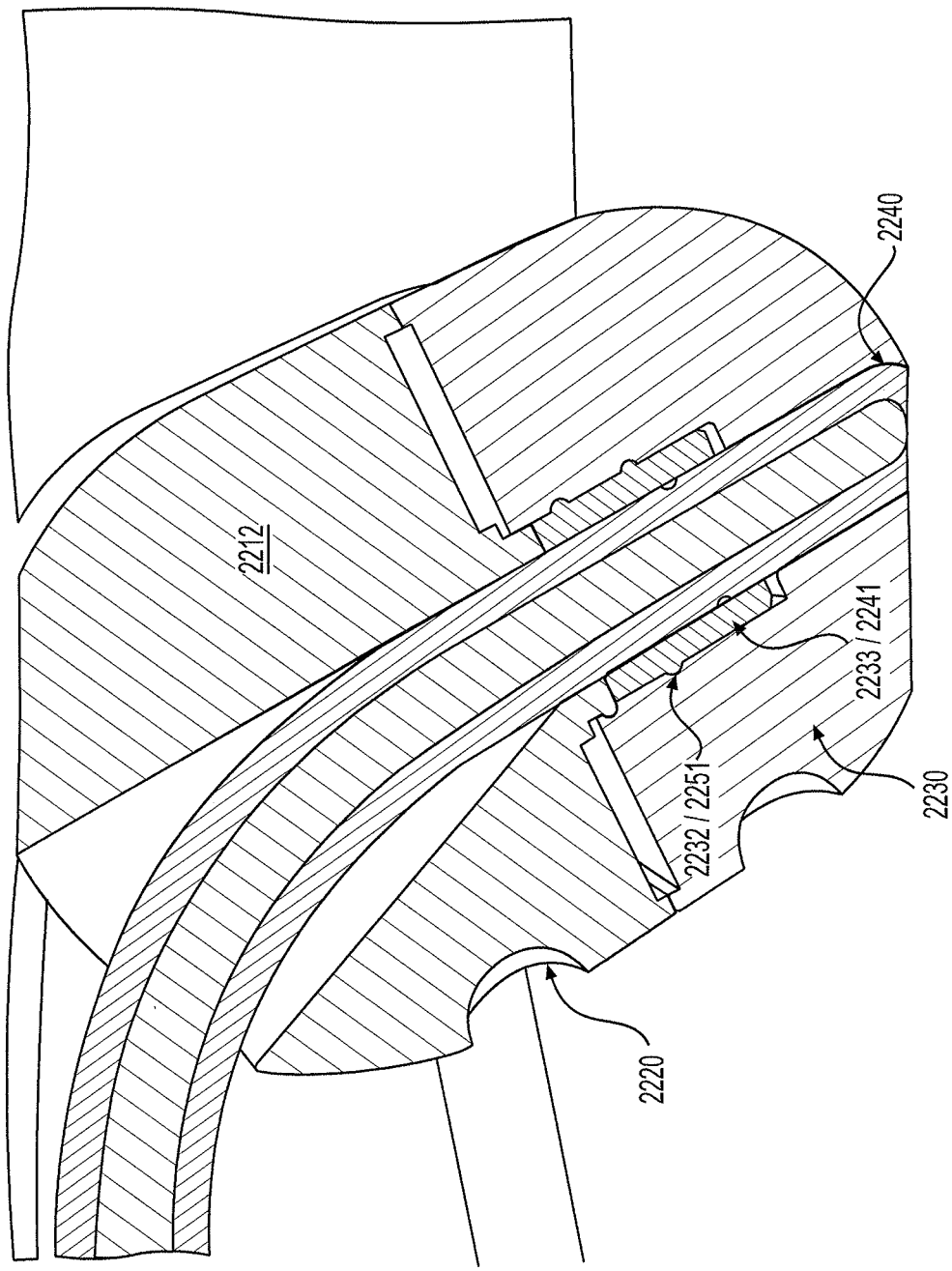

ADVANCED APPLICATOR SYSTEMS AND METHODS

CROSS-REFERENCE TO RELATED APPLICATIONS

This application is a National Stage Entry of International Application No. PCT/IB2015/002480, filed on Dec. 4, 2015, which claims the benefit of U.S. Provisional Patent Application No. 62/087,714, filed Dec. 4, 2014, and U.S. Provisional Patent Application No. 62/242,658, filed Oct. 16, 2015. The contents of the above-referenced applications application are expressly incorporated herein by reference in their entireties.

TECHNICAL FIELD

The present disclosure relates generally to radiation treatment systems and related methods. More particularly, and without limitation, the present disclosure relates to systems, methods, and devices to treat gynecological cancer.

BACKGROUND INFORMATION

Brachytherapy is a type of radiation therapy treatment for various cancers, such as gynecological cancer (e.g., cervical cancer, vaginal cancer, ovarian cancer, uterine cancer), for example. By applying various types of radiation to cancerous regions, cancerous cells are eliminated. To perform this kind of treatment, typically a physical applicator, which receives a radiation source for delivering radiation, is positioned adjacent to the cancerous tumor. For gynecological cancer, this involves inserting an applicator into the vagina to apply radiation treatment to gynecologic tumors. Additional radiation sources may be applied inside a cancerous tumor. Compared to external beam radiation therapies, locating the source of radiation in close proximity to the treatment site allows for targeted and efficient treatment of tumors, while limiting radiation dose to healthy tissue.

Applicators of existing systems include tubes embedded in basic shaped end pieces. The embedded tubes guide radiation sources to treatment locations. The tubes and end pieces may be shaped to provide specific radiation patterns to match treatment needs. For example, existing applicators include single-tube circular applicators and dual tube applicators.

Further, current systems for providing internal brachytherapy treatment have one or more limitations. Applicators often include many complex and small parts, which are difficult to assemble and maneuver. For example, fine, miniature screws are tedious to align and properly torque. The multitude of parts further complicates the use of the brachytherapy device after a treatment is performed, as the parts must be sterilized for subsequent uses. Keeping track of a swarm of small parts for sterilization adds a layer of complexity to the post-treatment process.

Accordingly, with conventional internal brachytherapy applicators, the user experience and efficiency of use may be degraded because the device is cumbersome and tedious to assemble and operate. Moreover, conventional applicators are difficult to maintain because the numerous parts are difficult to efficiently sterilize for subsequent uses. Therefore, there is a need for improved applicator assemblies.

SUMMARY

In accordance with embodiments of the present disclosure, systems, methods, and devices are provided for an advanced gynecological applicator. In accordance with some embodiments, a brachytherapy applicator is provided. The applicator may include two ovoid tubes configured to receive radiation sources. The two ovoid tubes may combine to form a rounded applicator having a middle opening. The applicator may also include a central applicator tube configured to receive a radiation source that is located within the middle opening. Each ovoid tube may have a matching curved end section.

In accordance with some embodiments, a brachytherapy applicator head and assembly is provided. The assembly may include two ovoid tubes configured to receive radiation sources, the two ovoid tubes combining to form a rounded applicator having a middle opening and comprising a plurality of needle holes to guide interstitial needles. The assembly may also include a central applicator tube configured to receive a radiation source that is located within the middle opening. Additionally, the assembly may include a vaginal cap that includes a tool-free connection to the two ovoid tubes and includes needle guides that align with the needle holes of the two ovoid tubes. The assembly may include a one-piece template for securing interstitial needles. The assembly may further include a tool-free connector to secure the two ovoid tubes to the central applicator tube.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate several embodiments and aspects of the present disclosure, and together with the description, serve to explain certain principles of the presently disclosed embodiments.

FIG. 2 illustrates diagrams analyzing example applicator shapes, consistent with embodiments of the present disclosure.

FIGS. 3A and 3B illustrate an example ring-shaped ovoid tube assembly, consistent with embodiments of the present disclosure.

FIGS. 4A, 4B, 4C, 4D, and 4E illustrate an example ring-shaped ovoid assembly including an interstitial tube guide, consistent with embodiments of the present disclosure.

FIG. 5 illustrates an example ring-shaped ovoid applicator assembly including interstitial needles, consistent with embodiments of the present disclosure.

FIGS. 7A, 7B, 7C, and 7D illustrate an example ring-shaped ovoid applicator assembly including a perineal template, consistent with embodiments of the present disclosure.

FIG. 21 illustrates an example alternative shape for an ovoid applicator, consistent with embodiments of the present disclosure.

FIGS. 22A, 22B, 22C, 22D, 22E, and 22F illustrate an example applicator assembly including an ergonomic ovoid, consistent with embodiments of the present disclosure.

DETAILED DESCRIPTION OF EXAMPLE EMBODIMENTS

Embodiments of the present disclosure will now be described. Example embodiments are described with reference to FIGS. 1-27, which may be implemented together or individually. The present disclosure generally relates to systems, methods, and devices for providing ring-shaped ovoid brachytherapy applicators.

Figure 1:
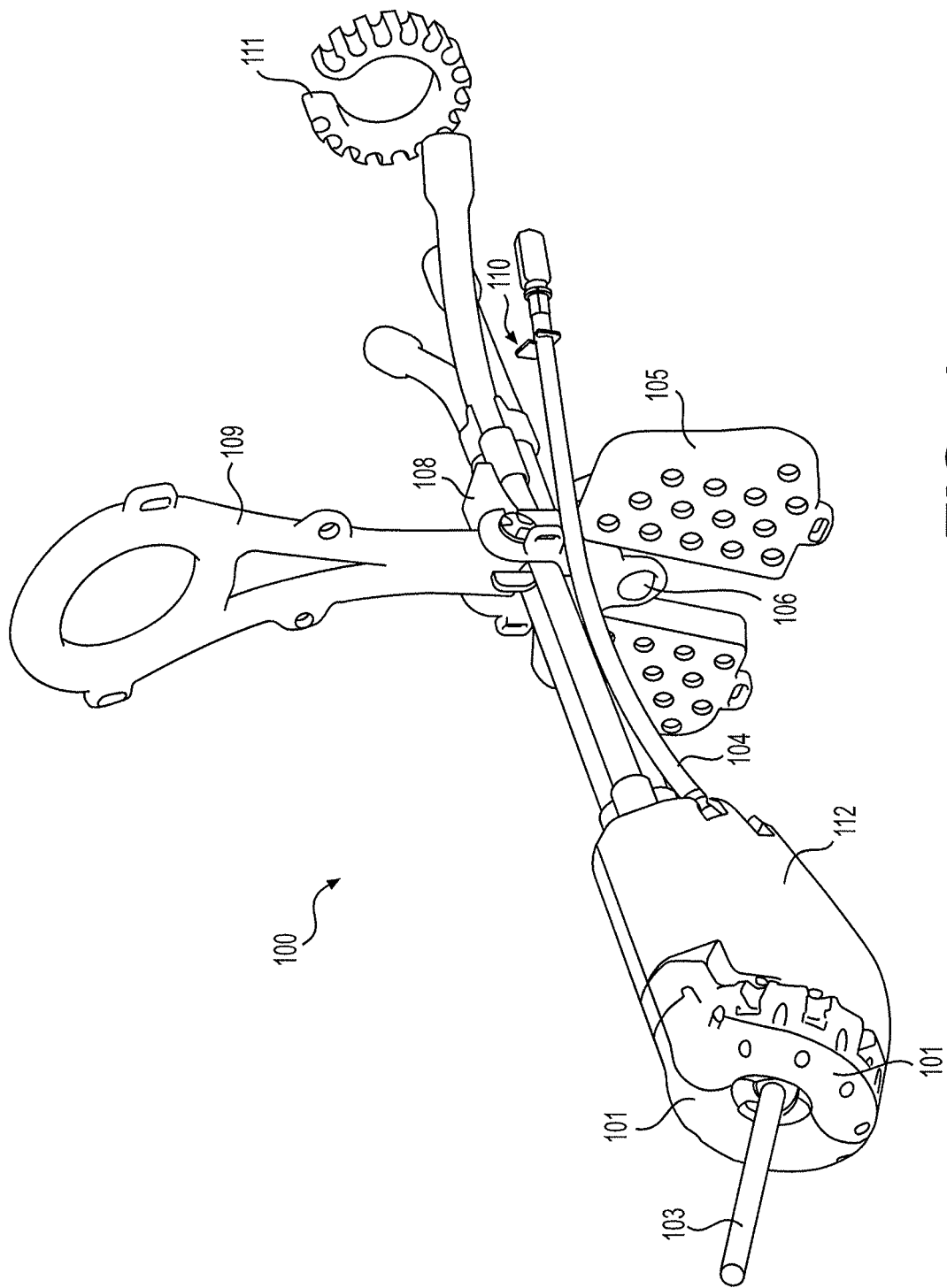
FIG. 1 illustrates an example ring-shaped ovoid applicator assembly, consistent with embodiments of the present disclosure.

FIG. 1 illustrates an example ring-shaped ovoid applicator assembly, consistent with embodiments of the present disclosure. Ring-shaped ovoid applicator assembly 100 is depicted in a particular configuration with certain accessories. However, various combinations of parts and mechanisms may be combined, added, or omitted consistent with this disclosure.

Ring-shaped ovoid applicator assembly 100 may include an applicator head portion to host radiation sources during a treatment session. In some embodiments, the head portion of the applicator may include multiple tubes to receive radiation sources, such as ring-shaped ovoid applicator head pieces 101 and central applicator tube 103 (e.g., an intrauterine tube, a vaginal tube). Although ring-shaped applicator head pieces 101 are depicted as being circular, the term "ring-shaped" may refer to any rounded geometry with in opening in its center. In some embodiments, shapes with any rounded geometry may be used (e.g., a square with rounded corners). Head pieces 101 may interlock to form, for example, a "doughnut" shape, an oval shape, a rounded square shape, or a teardrop shape. Other shapes without sharp or pointed edges may be used. The lock mechanism may be a tool-free mechanism that may permit users to interlock the pieces after inserting each piece individually into the patient. For example, rather than inserting the fully assembled applicator into the patient, the lock mechanism may permit a user to insert one of head pieces 101 into the patient, then insert the matching other half of head pieces 101 into the patient, and lock the two head pieces 101 together after they are inserted into the patient. By inserting each half the applicator head individually, a patient may experience less discomfort from the insertion of the applicator.

In some embodiments, the applicator head portion may include additional structure to shield organs that are not subject to treatment and guide supplemental radiation seeds. For example, vaginal cap 112 may connect to ring-shaped ovoid applicator head pieces 101 and include shielding to protect organs or treat tumors on a single side of a patient. For example, one half of vaginal cap 112 may include shielding while the other half does not. When a treatment site is located on one side of the patient, the shielded half of vaginal cap 112 may be used on the side opposite the treatment site to avoid irradiating tissue on that side.

In some embodiments, vaginal cap 112 may provide functions of a vaginal cylinder applicator. Vaginal cap 112 may hold back tissue (e.g., vaginal wall) to create space between radiation sources and tissue, which may prevent "hot spots" from occurring during treatment. Vaginal cap 112 may also provide functionality of a rectal retractor by pushing a patient's rectum away from the applicator. By securing organs and tissue at a distance from the path of the radiation sources, the applicator may avoid delivering a high dose or radiation to unintended treatment areas. In some embodiments, vaginal cap 112 may also hold radiation sources and secure needles in the vaginal wall during treatment.

In some embodiments, applicator tubes may be secured together. For example, head pieces 101 may include a locking mechanism to hold the two tube ends together. In some embodiments, as shown in FIG. 1, perineal connector 106 may secure or cradle multiple applicator tubes leading to ring-shaped ovoid applicator head pieces 101 and central applicator tube 103. Perineal connector 106 may include a mechanism to lock applicator tubes in place. For example, perineal connector 106 may include fixation clip 108. In some embodiments, fixation clip 108 may be designed to allow tool-free assembly. For example, the components of ring-shaped ovoid applicator assembly 100 may be assembled and secured by hand without the use of additional tools, such as hex keys, screw drivers, or pliers. In some embodiments, a tool-free assembly may be provided by fixation clip 108 being a lock lever, which holds applicator tubes together in perineal connector 106 using a friction fit. In other embodiments, alternative mechanisms may be used to secure applicator tubes together, such as a clip or snap-fit device, for example.

In some embodiments, ring-shaped ovoid applicator assembly 100 may support the placement of additional needles for more guidance of the radiation source. Ring-shaped ovoid applicator assembly 100 may include a plurality of sites to secure and guide interstitial needles. For example, larger tumors may require additional radiation source treatment sites in addition to central applicator tube 103 and ring-shaped ovoid applicator head pieces 101. Interstitial needles may be guided by additional mechanisms in ring-shaped ovoid applicator assembly. In some embodiments, ring-shaped ovoid applicator head pieces 101 and/or vaginal cap 112 may include connections to receive guiding tubes 104. Guiding tubes 104 may receive and route interstitial needles in which the radiation source can move to treatment sites.

In some embodiments, perineal connector 106 may connect to perineal template 105. Perineal template 105 may include a series of openings to guide interstitial needles. For example, perineal template 105 may include a grid pattern of openings to hold or host perineal needles as needed for treatment. Additional mechanisms may be included in ring-shaped ovoid applicator assembly 100 to secure and guide interstitial needles. For example, additional openings, guides, or templates, may attach to other locations of ring-shaped ovoid applicator assembly 100 as needed to route interstitial needles to additional treatment site locations.

Ring-shaped ovoid applicator assembly 100 may include structures and articles to organize applicator tubes and interstitial needles. In some embodiments, ring-shaped ovoid applicator assembly 100 may include labels or markers for different tubes or needles. Applicator tubes or interstitial needles may include markers, such as number tag 110, at the opening end of the tubes or needles. Such labels may ensure that operators connect the needles to the correct treatment tubes during treatment. For example, when ring-shaped ovoid applicator assembly 100 is placed inside a patient for treatment, the applicator head portion may not be visible. Thus, operators (e.g., physicians) may not be able to easily trace or otherwise determine where applicator tubes lead. Tube labels, such as number tag 110 may indicate which needle the tube leads to, for example, indicating to an operator the specific location at the end of the tube.

In some embodiments, additional structures may further organize needles or tubes in groups. Tube or needle brackets, such as bracelet 111, may include slots to hold multiple applicator tubes or interstitial needles. Tube or needle brackets may allow users to spatially organize tubes or needles based on user preferences or treatment procedures. While bracelet 111 is depicted as having a circular design with sites on the outer circumference to secure tubes, additional designs may be used. For example, securing locations may be located on the interior of the circumference instead of, or in addition to, the outer circumference sites. In other examples, securing sites may be oriented at different angles. In other embodiments, bracelet 111 may form a different shape than as shown in FIG. 1. For example, linear or polygon shapes may be used to secure tubes, such as a bar, a triangle, a square, pentagon, and octagon, for example. Polygons of additional number of sides may be used as well. In still other examples, other curved designs may be used, such as oval or u-shaped brackets. Curved and linear shapes may be combined in other bracket shapes without limit to meet design needs without limit.

In some embodiments, ring-shaped ovoid applicator assembly 100 may include handles to allow users to secure the applicator assembly to the patient's abdominal area. For example, ring-shaped ovoid applicator assembly 100 may include perineal bar 109 to orient and secure the assembly during treatment. Perineal bar 109 may thus provide a point to affix the assembly relative to the patient during treatment.

Ring-shaped ovoid applicator head pieces 101 provide benefits over existing applicator designs. FIG. 2 illustrates diagrams analyzing example applicator shapes, consistent with embodiments of the present disclosure. Circular applicators may better save critical organs in the posterior of the vagina. Additionally, circular ring applicators may provide a superior anatomical fit. For example, as shown in diagram 200, a circular applicator, such as that formed by ring-shaped ovoid applicator head pieces 101 may push vaginal wall 201 radially in all directions. Convention circular applicators, on the other hand, use a large single source tube that may be more difficult to insert into the patient and that may limit radiation treatment options.

Ovoid applicators, consistent with this disclosure, may resolve these problems. For example, ovoid applicators use two smaller tubes that allow easier insertion into the patient. Further, the multiple tubes permit additional treatment options by providing multiple locations for radiation sources. However, as shown in diagram 220, existing ovoid or tandem applicators 221 may permit vaginal wall 202 to move between the two separate ovoids. Crevices between ovoids prevent uniform radiation application as the vaginal wall may slide between two radiation sources.

In at least one embodiment, ring-shaped ovoid applicator head pieces 101 combine the advantages of circular ring applicators and ovoid applicators. For example, ring-shaped ovoid applicator head pieces 101 may retain the circular ring shape from two ring-shaped ovoid end pieces. Thus, ring-shaped ovoid applicator head pieces 101 may realize the benefits of the circular applicator shape, such as uniformly pushing back the vaginal wall and saving critical posterior organs (e.g., the rectum), as well as the benefits of the tandem and ovoid applicators two-tube design, such as being easier to insert into a patient and increasing treatment seed locations (e.g., asymmetrical radiation patterns). Additional benefits of ring-shaped ovoid applicator head pieces 101 may exist even though they are not specifically discussed in this disclosure.

Figure 3B:
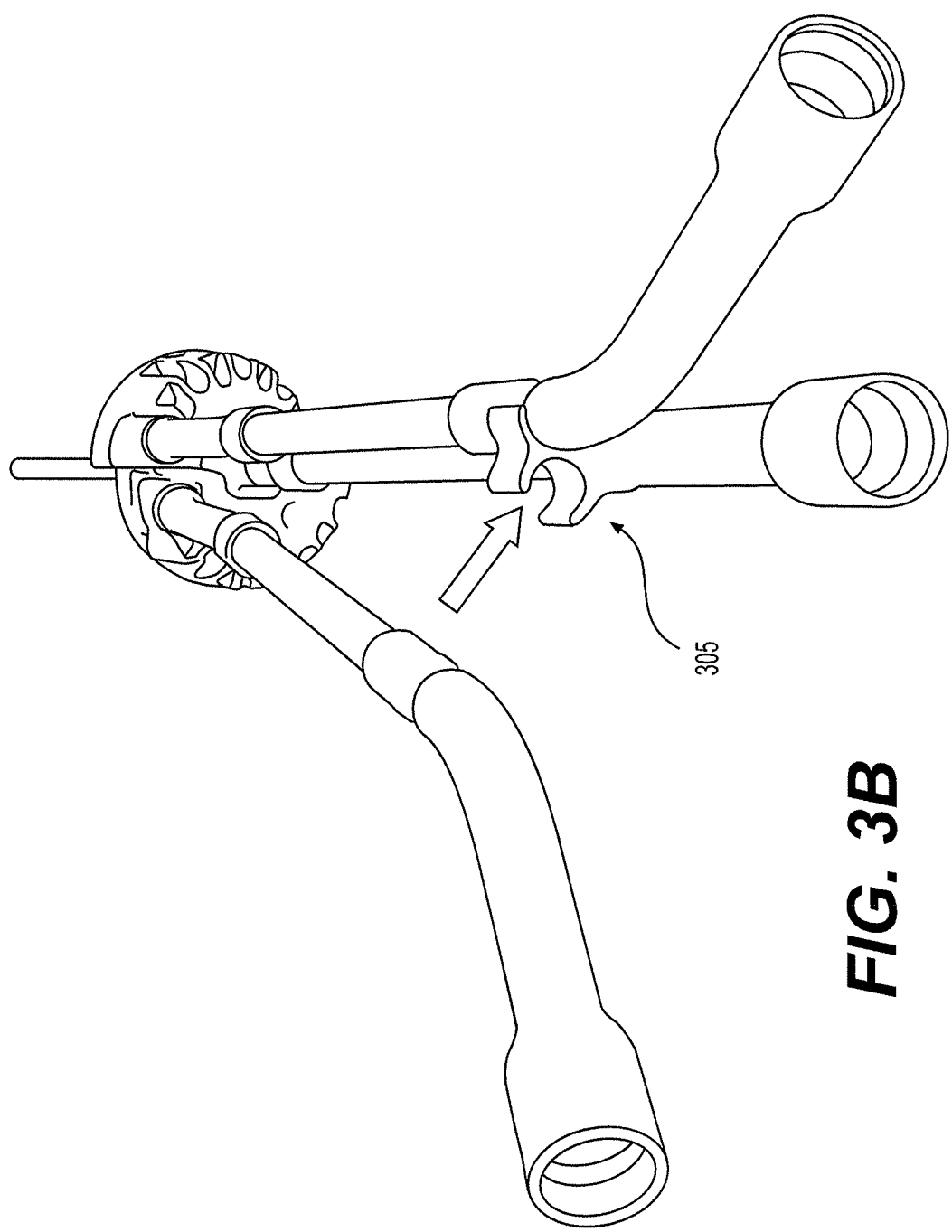

FIGS. 3A and 3B illustrate an example ring-shaped ovoid tube assembly, consistent with embodiments of the present disclosure. Ring-shaped ovoid applicator assembly 300 may include mechanisms to secure ring-shaped ovoid applicator head pieces 101 to central applicator tube 103.

In some embodiments, ring-shaped ovoid applicator head pieces 101 may utilize connections to (e.g., tube connections) structurally connect to central applicator tube 103. Ring-shaped ovoid applicator head pieces 101 may be connected to tubes, such as ring-shaped ovoid tubes 302 and 303. Central applicator tube 103 may include click mechanism 305 to receive and secure ring-shaped ovoid tubes 302 and 303. For example, click mechanism may be a snap-fit or friction-fit bracket which permits tool-free assembly. User may benefit from not needing tools to assemble the applicator. A medical setting may require tools to be sanitized, adding labor and additional steps to the assembly process. In other examples, a wrap or tape may be used alternatively, or in addition to, the snap-fit or fiction-fit to secure the applicator tubes. In still other examples, a screw or mechanical locking mechanism may be used, with or without tools to connect ring-shaped ovoid tubes 302 and 303 to central applicator tube 103. While FIGS. 3A and 3B depict a single click mechanism 305, some embodiments may use plural click mechanisms based on operational and structural needs.

In some embodiments, central applicator tube 103 may include additional or alternative mechanisms to secure ring-shaped ovoid applicator head pieces 101 to central applicator tube 103. Locking mechanism 304 may be attached towards the end of central applicator tube 103 to provide a securing mechanism at the applicator head end. Locking mechanism 304 may include slots or channels to receive and secure ring-shaped ovoid applicator head pieces 101. The channels or slots may provide a tool-free snap-fit or friction-fit connection.

Locking mechanism 304 may be used in combination with click mechanism 305. Locking mechanism 304 may ensure fixed applicator geometry during implantation, during treatment, and/or between treatments. Fixed geometry may permit consistent and predictable dose delivery to the patient because the location of the treatment positions with respect to the tumor are fixed. For example, as shown in FIG. 3B, central applicator tube 103 may be inserted into the uterus of the patient. Once central applicator tube 103 is located in the uterus, ring-shaped ovoid applicator head pieces 101 may slide or otherwise connect to locking mechanism 304 (e.g., one at a time). Then, as shown in FIG. 3B, click mechanism 305 may receive ring-shaped ovoid tubes 302 and 303. Additional combinations of connection mechanism may be used to connect ring-shaped ovoid applicator head pieces 101, ring-shaped ovoid tubes 302 and 303, and central applicator tube 103 consistent with this disclosure. By securing the applicator pieces together, users may more easily maneuver and insert ring-shaped ovoid applicator assembly 300.

In some embodiments, interstitial needles may provide additional treatment options. Interstitial needles may be inserted into the cervix, parametrium, and/or endometrium via the vagina. Anatomy may contain tumor tissue in gynecological cancers, such as, but not limited to the cervix, vaginal wall, parametrium, and endometrium. For example, tumor shapes, sizes, and locations may require guiding the radiation source to sites in addition to those in central applicator tube 103 and/or ring-shaped ovoid applicator head pieces 101. Interstitial needles may be plastic (e.g., medical-grade polymers) or metal (e.g., titanium).

Plastic needles may be less rigid. Accordingly, disclosed embodiments may include tube guides to receive and direct plastic tubes to target interstitial needle treatment sites. FIGS. 4A, 4B, 4C, 4D, and 4E illustrate an example ring-shaped ovoid assembly including an interstitial tube guide, consistent with embodiments of the present disclosure. Flexible needles may allow users for load the applicator with needles prior to inserting the applicator into the patient. Once inserted, the needles may be pushed forward, out of the applicator head piece and into the patient's tissue.

In some embodiments, ring-shaped ovoid applicator head pieces 101 may each have one or more interstitial needle openings 403. As shown, on the side facing the vaginal opening or towards the physician, ring-shaped ovoid applicator head pieces 101 may include tube slots to receive interstitial ring-shaped ovoid tube guide 402. While only a single tube guide is shown in FIG. 4A, ring-shaped ovoid applicator head pieces may receive multiple tube guides. Interstitial ring-shaped ovoid tube guides may include ends to match the cross section of the tube slots on the applicator head pieces. For example, the profile of the tube opening may be slightly smaller than the middle cross section of the tube end to form a snap-fit or friction-fit attachment to prevent lateral movement of the tubes. As shown, tube openings may include a ridge matching a corresponding circumferential notch in the tube ends to secure tube ends against the applicator.

Once interstitial ring-shaped ovoid tube guide 402 is secured to ring-shaped ovoid applicator head piece 101, interstitial needle 404 may be inserted into tube guide 402. While plastic needles are discussed as example interstitial needles used with tube guides, tube guide 402 may be used with any flexible needle. For example, certain metals or polymers may be used with tube guide 402. Finally, in some embodiments, the interstitial needle openings 403 may be used without guide tubes, in which case the physician inserts the interstitial needle directly through the opening.

In some embodiments, tube guide 402 may include mechanisms to secure interstitial needle 404 at a specific position along tube guide 402. For example, nut 405 may lock interstitial needle into a specific position. Nut 405 may provide tool-free operation by rotating about tube guide 402 to lock or unlock the position of interstitial needle 404. Additional needle locking mechanisms may be used to secure interstitial needle in tube guide 402. For example, a circumferential plug may be used to provide a friction fit.

In an exemplary method, tube guide 402 and interstitial needle 404 may be complete assembled before insertion into the patient. For example, tube guide 402 may be secured to ring-shaped ovoid applicator head pieces 101 prior to insertion into the patient. Interstitial needle 404 may be inserted into tube guide 402, locked in a position just below interstitial needle opening 403. Once inserted into the patient, nut 405 may be loosened or unlocked, and interstitial needle 404 may be moved forward into the treatment site (e.g., into the cervix or parametrium). Once in the final treatment location, interstitial needle 404 may be locked in place again using nut 405. While this exemplary method has been discussed, steps may be modified or performed in different orders to suit treatment requirements without limit.

Figure 4C:
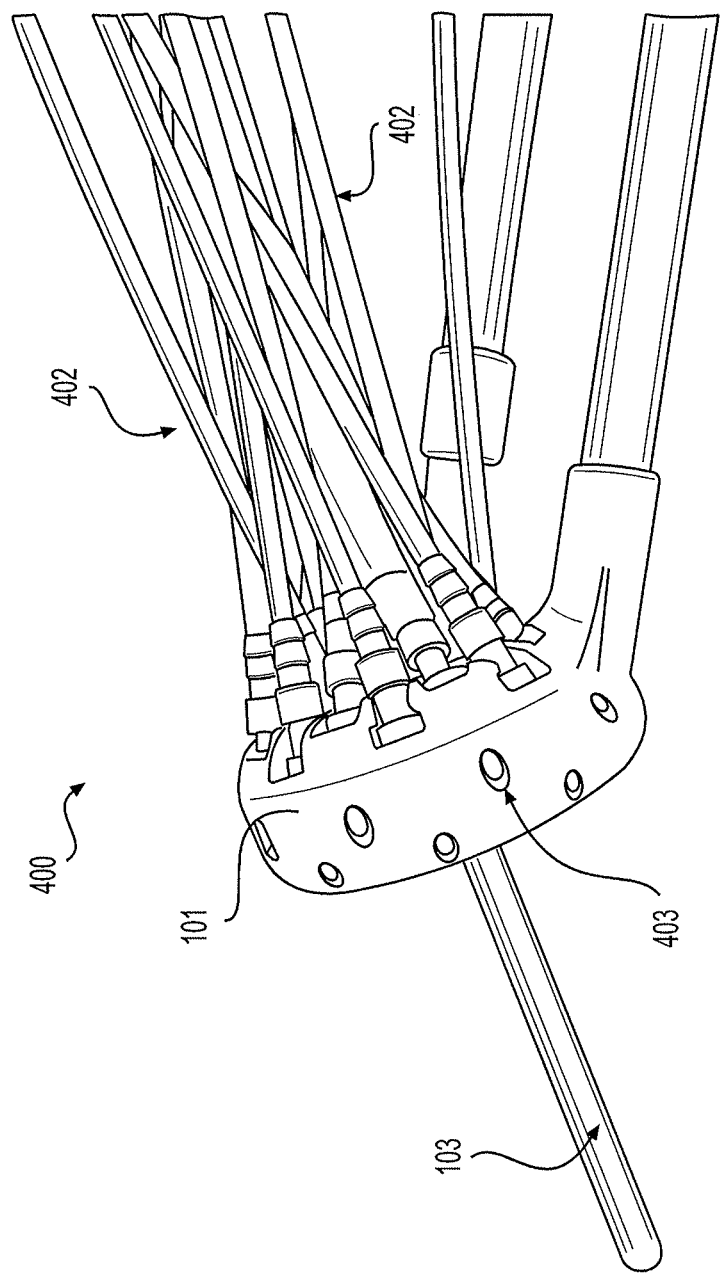
Figure 4E:
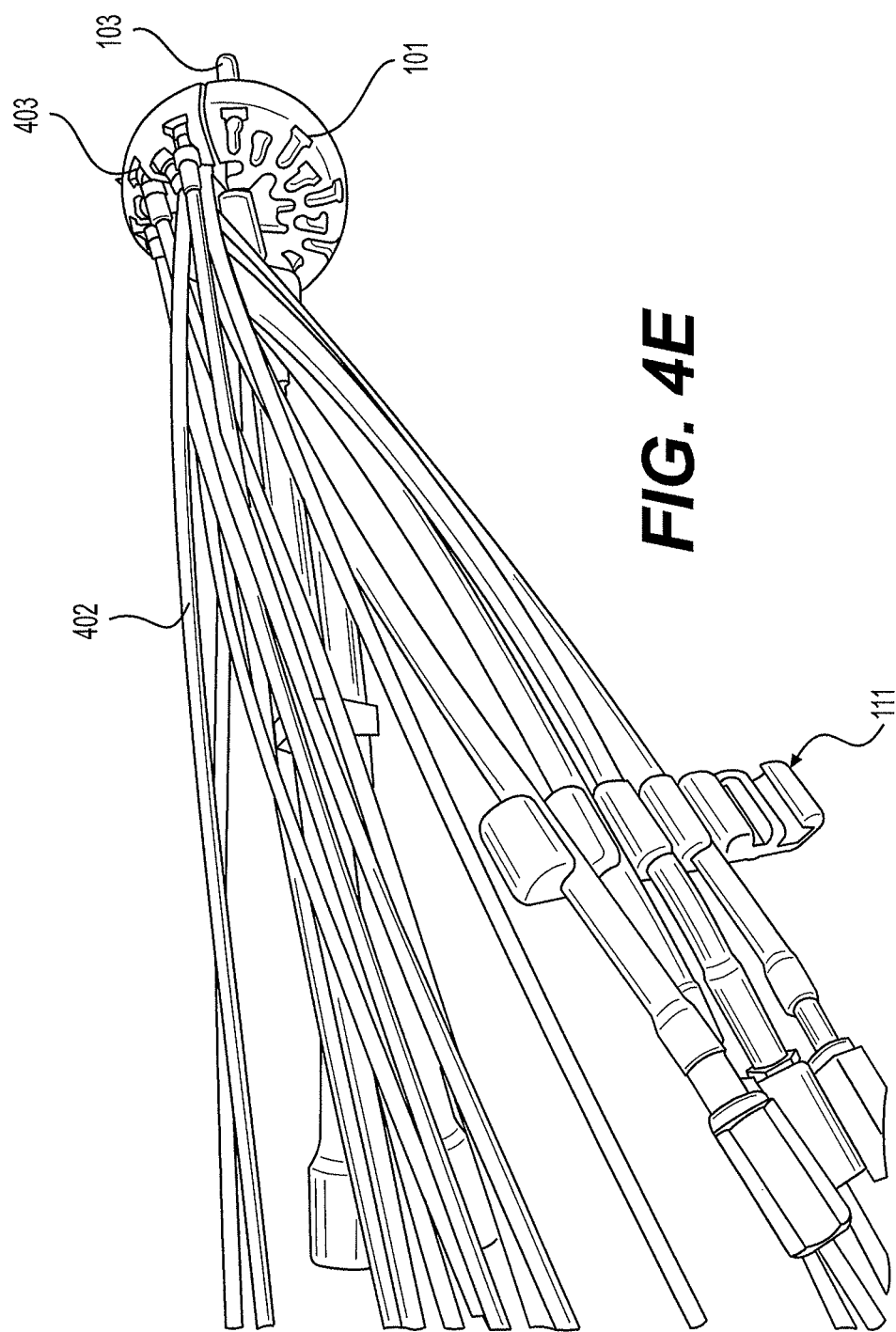

As shown in FIG. 4E, one or more of tube guides 402 may be secured together. Bracelet 111 may secure and organize tube guides 402 at an end opposite head piece 101. For example, bracelet 111 may include labeled brackets to hold tubes in a particular spatial arrangement. As shown in FIG. 4E, bracelet 111 is structured to provide a linear arrangement, though bracelet 111 may be formed in a different shape to provide tube slots (e.g., mounting points or securing locations) that form a circular, oval, or rectangular patter, for example.

Disclosed embodiments may also utilize rigid needles. For example, needles may be made of metal (e.g., titanium). FIG. 5 illustrates an example ring-shaped ovoid applicator assembly including rigid interstitial needles, consistent with embodiments of the present disclosure. Ring-shaped ovoid applicator assembly 500 may include one or more rigid needles 501. For example, interstitial needle opening 403 may receive both flexible and rigid needles. Interstitial needle openings may orient needles in a specific direction. For example, openings may be angled to create oblique interstitial needle 503. Alternatively, openings may run parallel to central applicator tube 103 to align parallel interstitial needle 502. Additional angles or locations for interstitial needle openings may be used.

In an exemplary method, central applicator tube 103 and ring-shaped ovoid applicator head pieces 101 may be assembled and inserted into the patient as previously discussed. After insertion into the patient, rigid needles 501 may be inserted into the parametrium and/or cervix via the needle openings in ring-shaped ovoid applicator head pieces 101. Once inserted into the patient, rigid needles 501 may be secured using, e.g., tape, a locking mechanism, or a bracket.

Figure 6B:
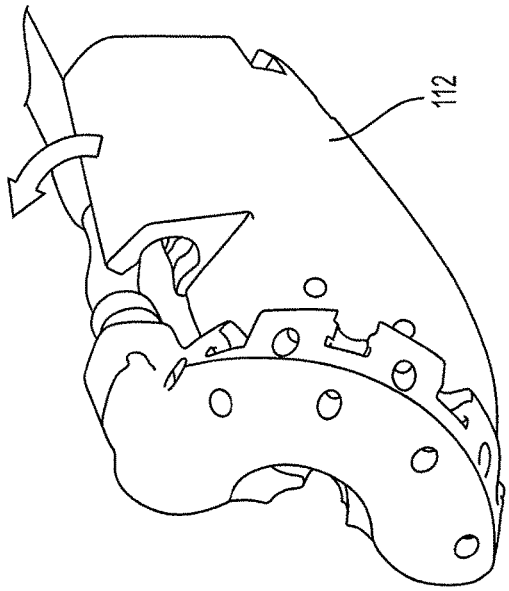
FIGS. 6A, 6B, 6C, and 6D illustrate an example ring-shaped ovoid applicator head assembly including a vaginal cap, consistent with embodiments of the present disclosure.
Figure 6D:
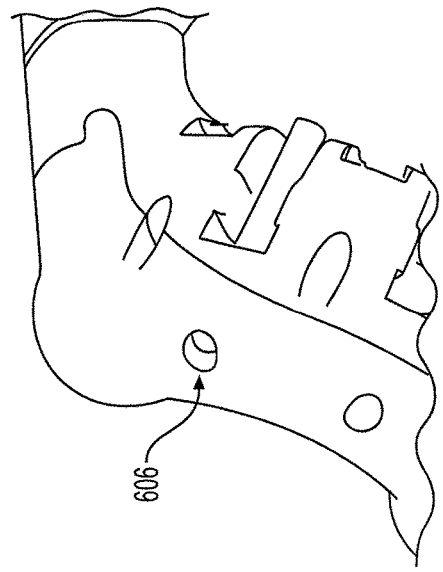
Figure 6A:
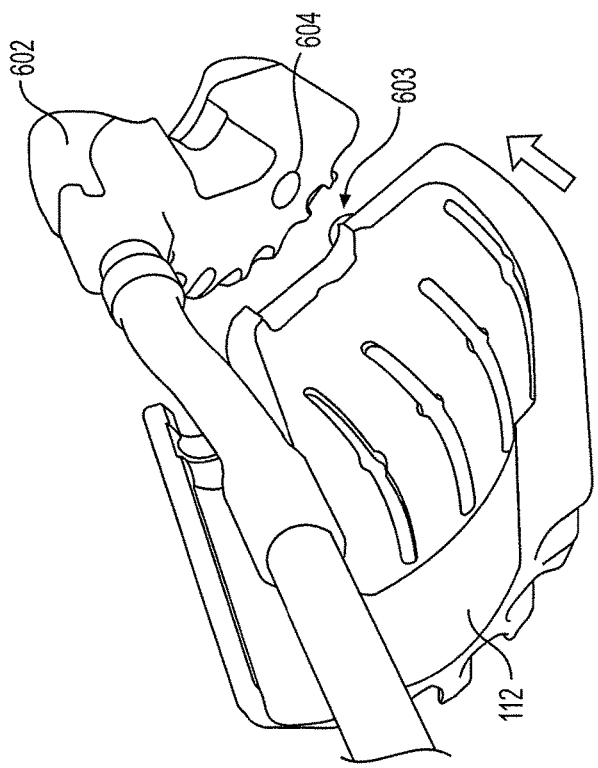

FIGS. 6A, 6B, 6C, and 6D illustrate an example ring-shaped ovoid applicator head assembly including a vaginal cap, consistent with embodiments of the present disclosure. In some embodiments, vaginal cap 112 may connect to ring-shaped ovoid applicator head piece 602 (e.g., ring-shaped ovoid applicator head pieces 101). As shown in FIG. 6A, vaginal cap 112 may include alignment pin 603, which may be received by alignment hole 604 on the back side of ring-shaped ovoid applicator head piece 602. Alignment pin 603 and alignment hole 604 may include a connection mechanism. For example, alignment pin 603 may include a circumferential ridge to provide a tool-free snap-fit or friction-fit connection with alignment hole 604. In other examples, alignment pin 603 may be a smooth cylinder that provides axial alignment with alignment hole 604, but may slide and rotate freely within alignment hole 604.

Once alignment pin 603 is inserted into alignment hole 604, vaginal cap 112 may rotate about the alignment pin connection. As shown in FIG. 6B, vaginal cap 112 may include an opening to receive an ovoid tube (e.g., ring-shaped ovoid tube 303). The opening of vaginal cap 112 may provide snap-fit or click-fit tool-free connection. When secured, vaginal cap 112 may include one or more paths aligning with interstitial needle openings on ring-shaped ovoid applicator head pieces 101.

Figure 6C:
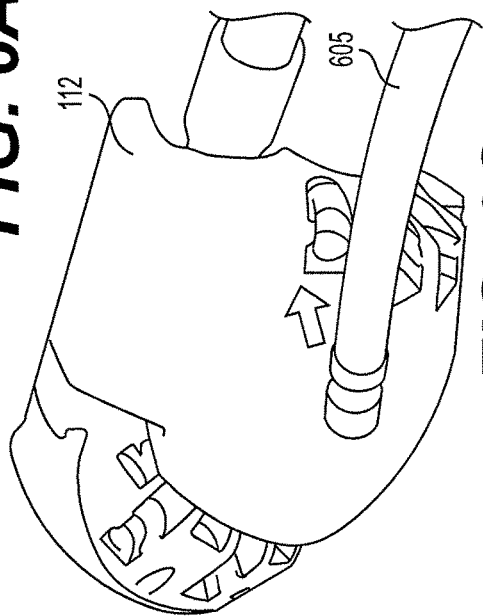

In some embodiments, guide tubes may connect to vaginal cap 112, rather than directly to ring-shaped ovoid applicator head pieces 101. As shown in FIG. 6C, vaginal cap 112 may include slots to receive guide tube 605. The receiving slots may function similar to those of interstitial needle opening 403 described above. When guide tube 605 is connected, vaginal cap 112 may receive interstitial needles from guide tube 605. Method steps for inserting needles may follow the same steps outlined above with respect to FIGS. 4A, 4B, 4C, 4D, and 4E (e.g., interstitial needles may be preloaded and locked below the surface of openings; after the applicator is inserted into the patient, interstitial needles may be pushed through to the cervix). Vaginal cap 112 may include additional channels to guide interstitial needles to interstitial needle opening 606 of ring-shaped ovoid applicator head piece 101. In some embodiments, vaginal cap may include additional openings to guide interstitial needles directly to treatment sites without passing through ring-shaped ovoid applicator head piece 101. For example, vaginal cap 112 may include opening to pass needles to treat vaginal disease.

FIGS. 7A, 7B, 7C, and 7D illustrate an example ring-shaped ovoid applicator assembly including a perineal template, consistent with embodiments of the present disclosure. A perineal template may provide additional potential needle sites.

Ring-shaped ovoid applicator assembly 700A may add perineal connector 106. In some embodiments, perineal connector 106 may include perineal connector base 701 that may cradle or otherwise hold (e.g., circumferential pinch) ring-shaped ovoid tubes 302 and 303, as well as central applicator tube 103. Perineal connector 106 may also include perineal connector lever 702. Perineal connector lever 702 may slide along the length of ring-shaped ovoid tubes 302 and 303 into perineal connector base 701.

Once perineal connector base 701 and perineal connector lever 702 is positioned against the perineum, perineal connector 106 may be locked into position by lowering perineal connector lever 702, as shown in FIG. 7B. Perineal connector lever 702 may provide a friction-fit connection against ring-shaped ovoid tubes 302 and 303.

Ring-shaped ovoid applicator assembly 700B may include perineal template 105. In some embodiments, perineal template 105 may be received by a matching opening in perineal connector base 701. Locking screw 704 may hold perineal template 105 in place. A user may rotate locking screw 704 (e.g., 90 or 180 degrees) to engage a friction fit, setting the angle of perineal template 105 with respect to ring-shaped ovoid tubes 302 and 303. In other embodiments, additional locking mechanism may be used. For example, alternative embodiments may use a fixation clip instead of a locking screw.

In some embodiments, perineal template 105 may be made of a single piece of material. For example, perineal template 105 may be molded and/or milled from a single piece of plastic or metal.

Ring-shaped ovoid applicator assembly 700C may receive needles through template 105. In some embodiments, needle lock insert 705 may fit into an opening of perineal template 105. Needle 706 may be inserted into the fitted needle lock insert 705. In other embodiments, needle lock insert may be place on needle 706. The combination of needle 706 and needle lock insert 705 may then be threaded through perineal template 105. In still other embodiments, there may be no need for a lock insert. For example, the needles may be locked by friction, screws, or snap-fit connections.

Ring-shaped ovoid applicator assembly 700D may secure needles. Once needle 706 and needle lock insert 705 are positioned in perineal template 105, needle lock insert may be engaged by rotating needle lock insert (e.g., 90 or 180 degrees), as shown as rotation motion 708. For example, a lock tool, such as a small wrench or key, may be used to rotate needle lock insert. In some embodiments, lock insert 705 may be designed to provide tool-free locking. For example, lock insert may include wing nut extensions to permit toll-free rotation. Other locking mechanisms may be used consistent with this disclosure.

Figure 8:
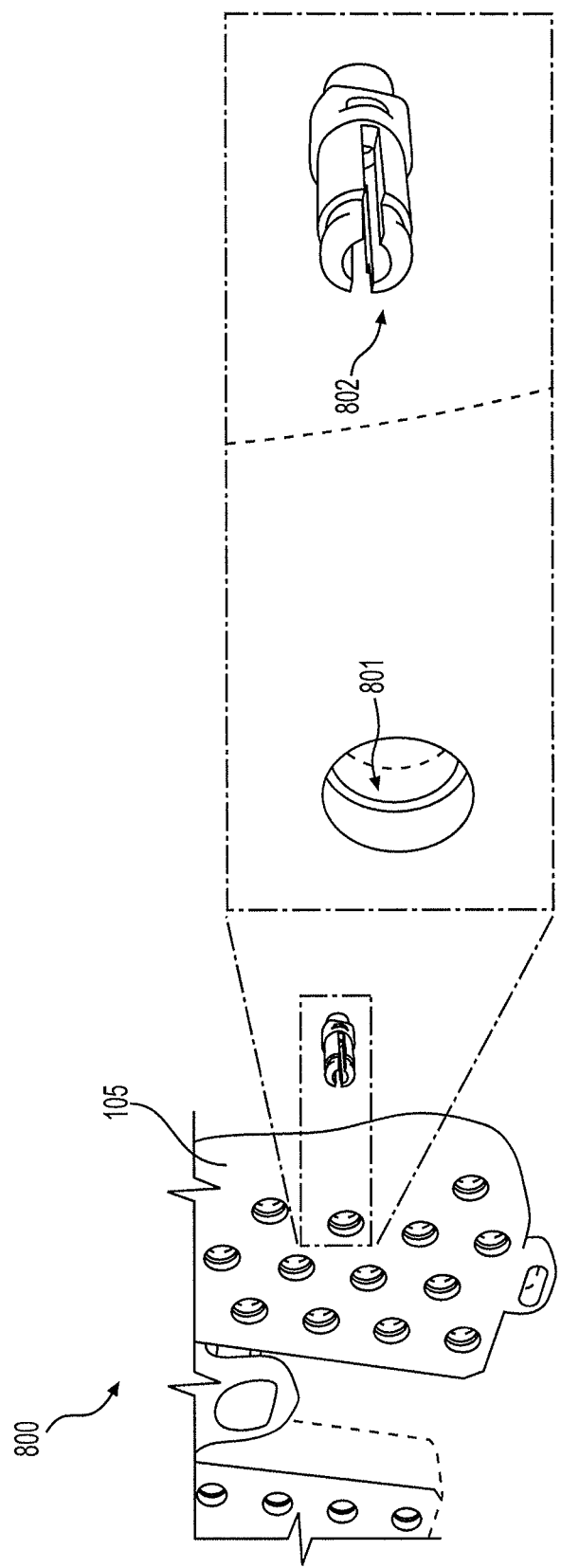
FIG. 8 illustrates an example perineal template assembly, consistent with embodiments of the present disclosure.

FIG. 8 illustrates an example perineal template assembly, consistent with embodiments of the present disclosure. As shown, perineal template assembly 900 may include a series of template lock openings 801. In some embodiments, template lock openings 801 may include a ridge or threading to secure needles in place. Lock insert 802 may include a cylindrical ridge to engage template lock openings 801.

As shown, in some embodiments, lock inserts may have material removed to allow the sides of the lock insert 802 to bend inward. For example, when lock insert 802 is engaged in locking, lock insert 802 may be driven into template lock opening 801 which applies pressure to the sides of lock insert 802. Lock insert 802 in turn, applies pressure from its inner circumference to the outer circumference of the needle, forming a friction fit between the inner face of lock insert 802 and the outer surface of the needle.

Figure 9A:
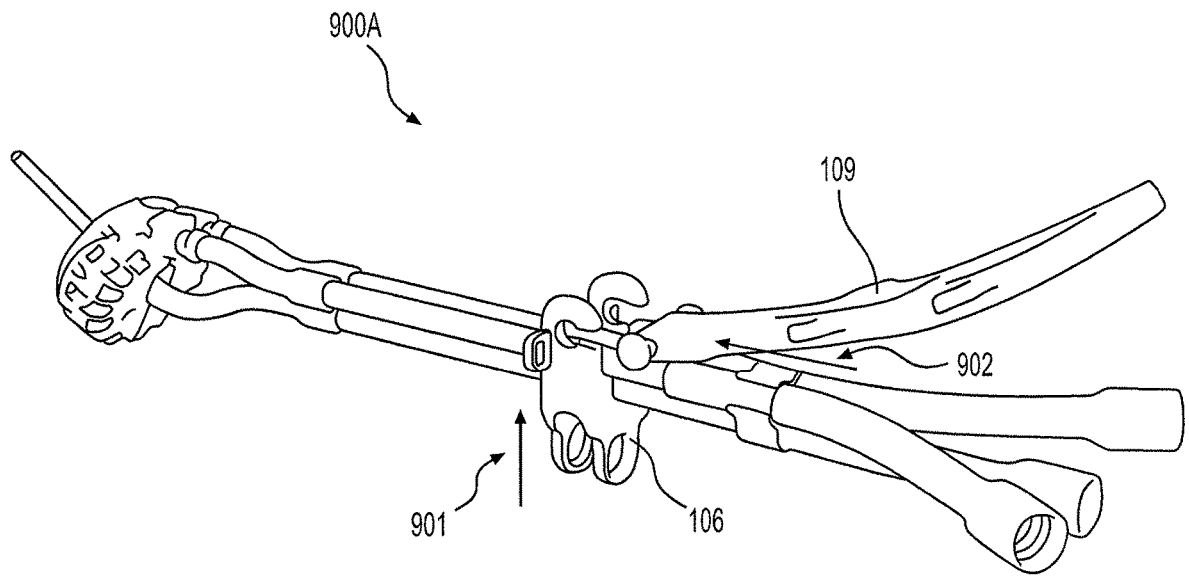
FIGS. 9A and 9B illustrate an example ring-shaped ovoid applicator assembly with a perineal bar, consistent with embodiments of the present disclosure.
Figure 9B:
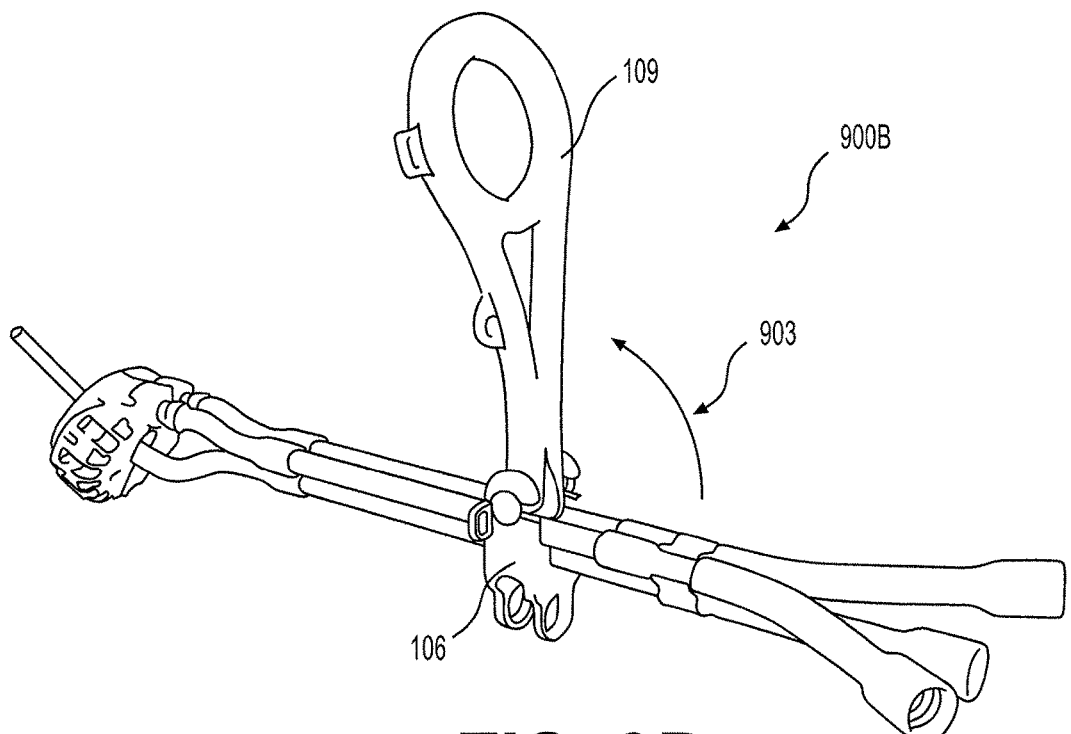

FIGS. 9A and 9B illustrate an example ring-shaped ovoid applicator assembly with a perineal bar, consistent with embodiments of the present disclosure. In some embodiments, instead of, or in addition to, using a clip or small lever, perineal clip may be used to secure applicator tubes together (e.g., central applicator tube 103 and ring-shaped ovoid tubes 302 and 303).

As shown in FIG. 9A, perineal connector 106 may move in vertical motion 901 to cradle central applicator tube 103 and ring-shaped ovoid tubes 302 and 303. Then, perineal bar 109 may be aligned parallel to the applicator tubes and moved in horizontal slide motion 902 into the corresponding clips of perineal connector 106. Perineal bar 109 may be connected to perineal connector using a snap-fit or click-fit connection, for example.

As shown in FIG. 9B, perineal bar 109 may be rotated to a vertical position using rotation motion 903. Rotation motion 903 may cause perineal bar 109 to exert additional force on the applicator tubes, forming a friction-fit connection. Perineal connector 106 and/or perineal bar 109 may include a stop to prevent perineal bar from rotating past a certain angle or applying excessive pressure on the applicator tubes. For example, a mechanical stop may block perineal bar from rotating past 90 degrees.

Figure 10:
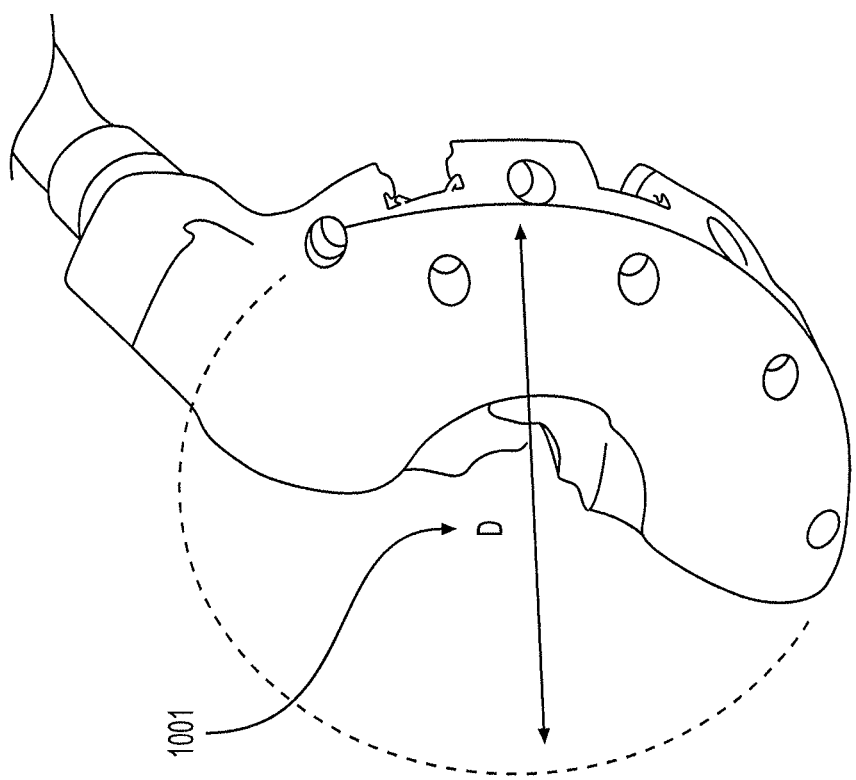
FIG. 10 illustrates an example ring-shaped ovoid applicator head, consistent with embodiments of the present disclosure.

FIG. 10 illustrates an example ring-shaped ovoid applicator head, consistent with embodiments of the present disclosure. Two ring-shaped ovoid applicator head pieces 101 may be combined for form a complete doughnut shape. In some embodiments, the distance of the source path to the surface of the applicator may be in the range of 3 to 15 mm to the distal and lateral side of the applicator. In some embodiments, the ring-shaped ovoid applicator head may be sized based on its outer diameter 1001. For example, based on standard anatomy size distribution, ring-shaped ovoid applicator head pieces 101 may be sized to match predetermined outer diameters chosen to fit into the vaginal fornix. Each outer diameter size may have a single corresponding inner diameter ranging from 15 to 60 mm. For example, exemplary outer diameters and their exemplary corresponding source path diameters are shown below in Table 1:

TABLE 1

| Diameter of source path (mm) | Outer Diameter (mm) |
| --- | --- |
| 22 | 34 |
| 26 | 38 |
| 30 | 42 |

Though, in some embodiments, a given outer diameter size may have multiple potential inner diameters. In other embodiments, outer diameter 1001 may be customized to match outlier anatomy dimensions. Known manufacturing techniques (e.g., three-dimensional printing, molding, milling, etc.) may be used to provide customized pieces.

Ring-shaped ovoid applicator head pieces 101, tubes, and other pieces of the disclose assemblies may be made of plastic materials. For example, ring-shaped ovoid applicator head pieces 101 may be made by plastic injection molding, three-dimensional printing (e.g., additive polymer printing), or milling plastic components to the desired shape.

Figure 11:
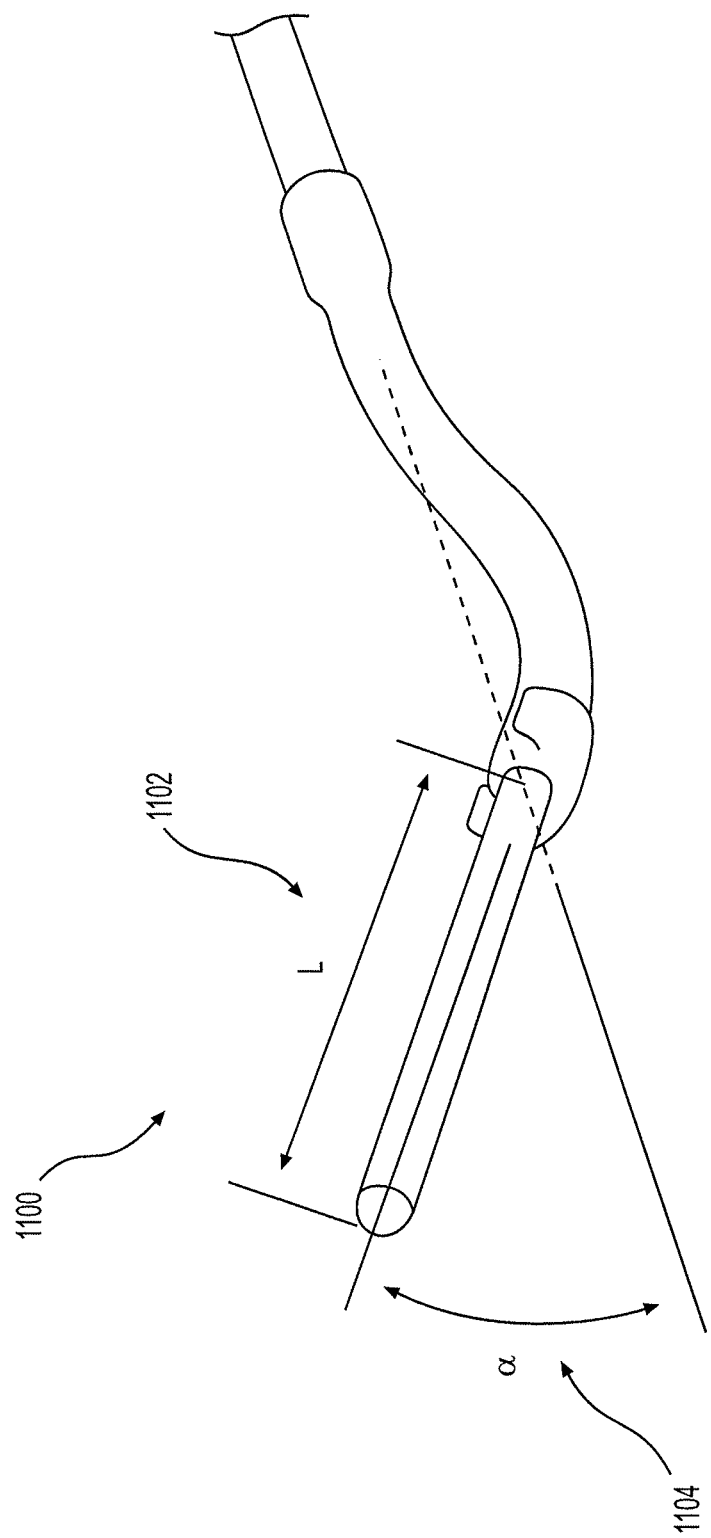
FIG. 11 illustrates an example intrauterine tube, consistent with embodiments of the present disclosure.
Figure 12:
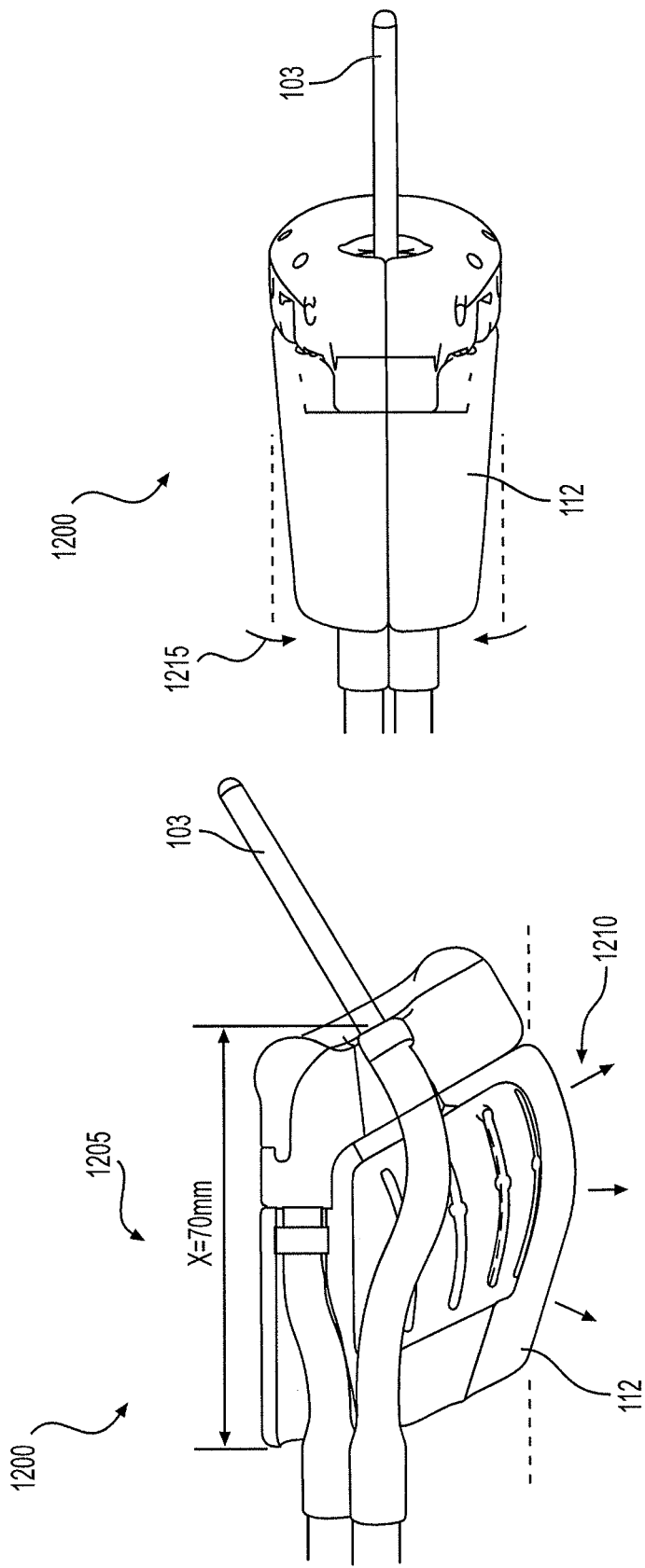
FIGS. 12A and 12B illustrate an example ring-shaped ovoid applicator head assembly including a vaginal cap, consistent with embodiments of the present disclosure.

FIG. 11 illustrates an example central applicator tube, consistent with embodiments of the present disclosure. In some embodiments, central applicator tube 1100 (e.g., central applicator tube 103) may be shaped based on its length 1102 and tube angle 1103. For example, based on standard anatomy size distribution, central applicator tubes may be sized to match predetermined lengths at certain angles (e.g., angles offset from the lead tube, as shown in FIG. 11). Each length may have multiple corresponding angles. For example, exemplary lengths and their exemplary corresponding angles are shown below in Table 2:

TABLE 2

| Length (mm) | Angles (degrees) |
| --- | --- |
| 30 | 30, 15 |
| 40 | 30, 15 |
| 50 | 30, 15 |

TABLE 2-continued

| Length (mm) | Angles (degrees) |
| --- | --- |
| 60 | 30, 15 |
| 70 | 30, 15 |

Though, in some embodiments, a given length may only be available in a single angle. In other embodiments, length 1102 and/or angle 1104 may be customized to match outlier anatomy dimensions. In other embodiments, lengths may range from 0 to 100 mm, and angles may range from 90 to −90 degrees.

In some embodiments, central applicator tube may be 2.5 to 7 mm in diameter. An exemplary central applicator tube may be 4 mm in diameter. This exemplary diameter balances the benefits of a smaller tube (e.g., lower uterus dilation requirement) against the risks associated with a smaller diameter tube (e.g., increased chance of perforating the uterus). However, a given patient's anatomy may require a different tube diameter. In some embodiments, the central applicator tube may include a truncated or shortened central applicator tube to apply radiation treatments for patients that have had a hysterectomy. While a diameter has been discussed, the central applicator tube 103 may not be limited to a circular shape. In some embodiments, central applicator tube 103 may have an oval or flattened cross-section.

FIGS. 12A and 12B illustrate an example ring-shaped ovoid applicator head assembly 1200 including vaginal cap 112, consistent with embodiments of the present disclosure. As shown in FIGS. 12A and 12B, vaginal cap 112 may be designed match a standard anatomical fit of patients. For example, an exemplary length 1205 of vaginal cap 112 may be 70 millimeters. In certain embodiments, vaginal cap may include a conical design based on taper 1215 to fit the anatomy of the vagina. In some embodiments, vaginal cap 112 may include functionality of a rectal retractor by holding the rectum at a distance from the radiation source. For example, vaginal cap 112 may block radiation in the direction of the rectum (e.g., directions 1210) during treatment.

Figure 13:
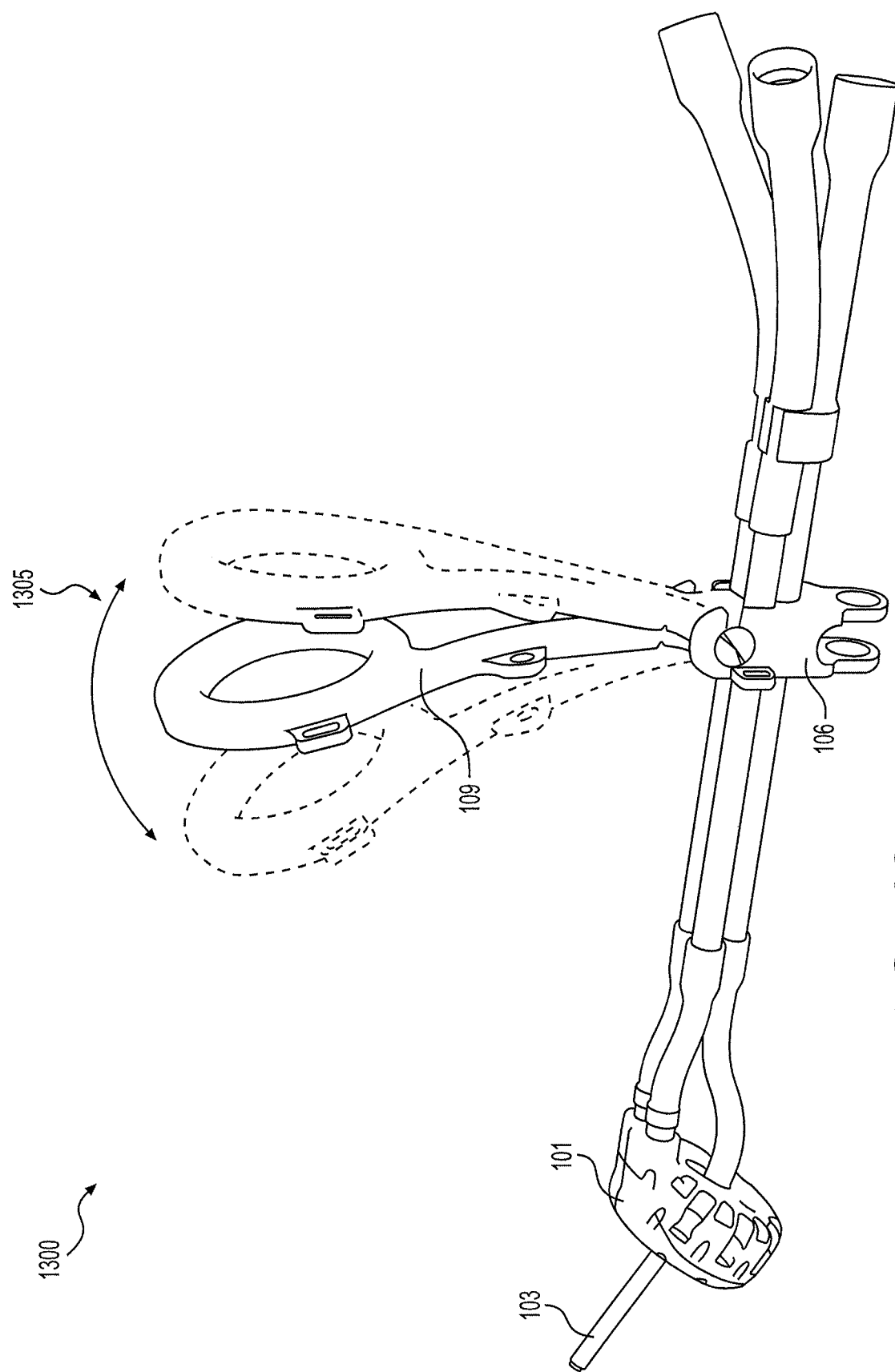
FIG. 13 illustrates an example ring-shaped ovoid applicator assembly with a perineal bar, consistent with embodiments of the present disclosure.

FIG. 13 illustrates an example ring-shaped ovoid applicator assembly with a perineal bar, consistent with embodiments of the present disclosure. As shown in FIG. 13, perineal connector may be configured to permit angular adjustments 1305 of perineal bar 109. In certain embodiments, angle stops may prevent perineal bar from rotating past a certain angle. For example, patient safety or comfort may be inhibited at extreme angles.

Figure 14:
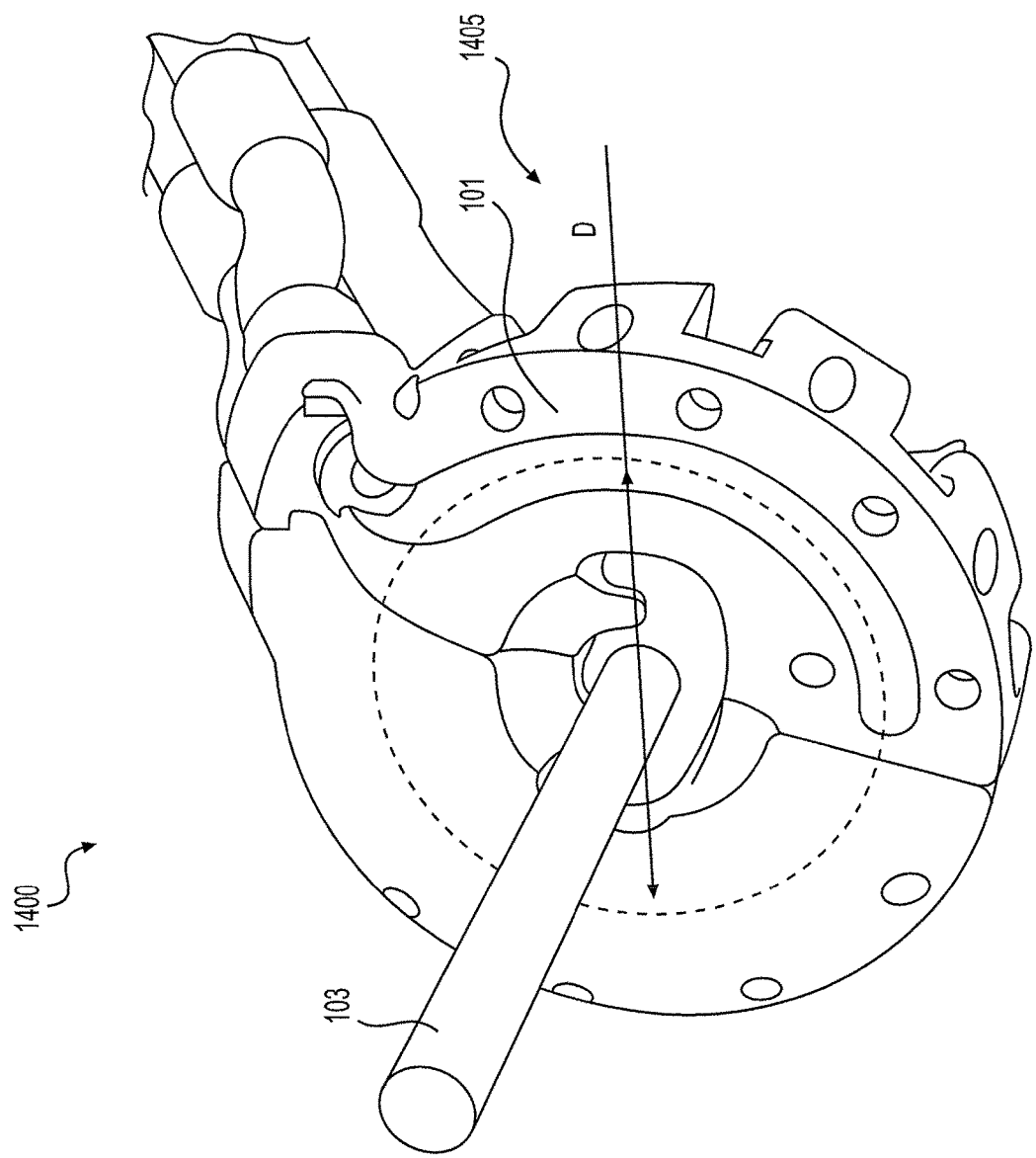
FIG. 14 illustrates an example ring-shaped ovoid applicator head assembly, consistent with embodiments of the present disclosure.

FIG. 14 illustrates an example ring-shaped ovoid applicator head assembly 1400, consistent with embodiments of the present disclosure. As shown in the cross sectional view of FIG. 14, ring-shaped ovoid applicator head pieces 101 may include an embedded ring-shaped ovoid tube. For example, the "doughnut" formed by ring-shaped ovoid applicator head pieces 101 may include a hollow channel to receive the radiation source.

In an exemplary embodiment, the ring-shaped ovoid tube may be embedded with 6 millimeters of material surrounding all sides of the tube to provide a homogeneous radiation does to surrounding tissue. In some embodiments, the source path of the ring-shaped ovoid tube may be positioned under an angle of 60 degrees measure from the vaginal axis to the cervix to fit common anatomy. Additional angles and thicknesses may be used for the applicator head to meet patient needs consistent with this disclosure.

Figure 15:
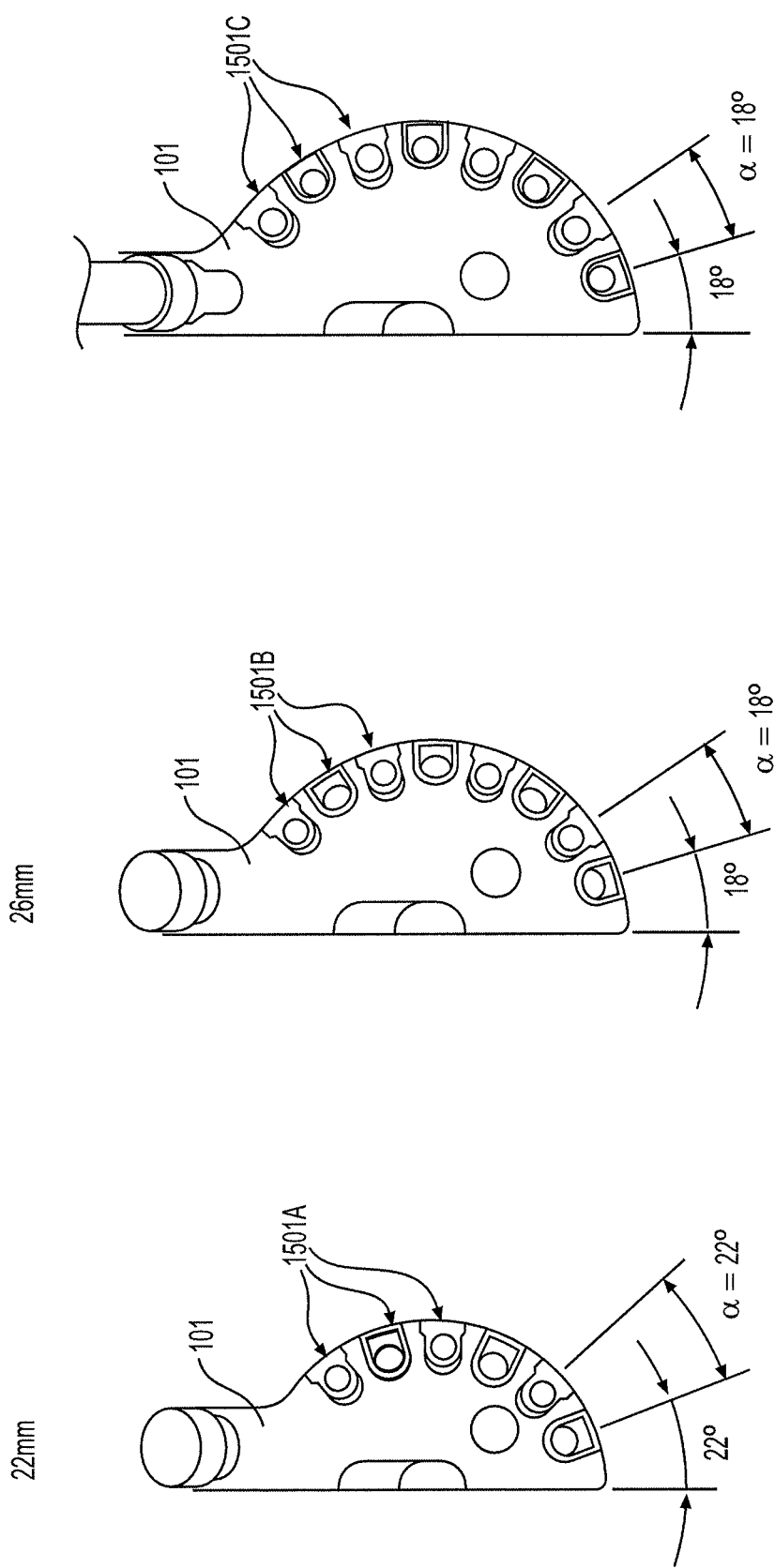
FIG. 15 illustrates example ring-shaped ovoid applicator head assemblies, consistent with embodiments of the present disclosure.

FIG. 15 illustrates example ring-shaped ovoid applicator head assemblies, consistent with embodiments of the present disclosure. As shown in FIG. 15, ring-shaped ovoid applicators having different diameters may include different numbers of interstitial needle sites. For example, a 22 millimeter diameter head may include 6 interstitial needle sites 1501A on each half spaced 22 degrees apart. In other examples, a 26 millimeter diameter head and a 30 millimeter diameter head may both have 8 interstitial needles sites (sites 1501B and 1501C) on each half spaced 18 degrees apart. The smaller applicator head sizes may not have the space to accommodate as many interstitial needle sites.

In some embodiments, interstitial needle sites may orient needles in different directions. For example, openings may direct interstitial needles parallel to the central applicator tube or oblique to the central applicator tube, offset by a certain angle. As shown in FIG. 15, in an example embodiment, the oblique interstitial needle sites may alternate with parallel interstitial needle sites to provide an increased number of variations to reach the maximum number of potential treatment locations. Additional interstitial tube site arrangements may include additional angles or sequences of site types on the applicator head. For example, the sites may not necessarily be evenly spaced.

In some embodiments, head pieces may include openings for interstitial needles at irregular or asymmetrical positions. For example, one head pieces may have three openings for interstitial needles while the other half has no openings. In some embodiments, both of head pieces 101 may not include any interstitial needle openings.

Figure 16:
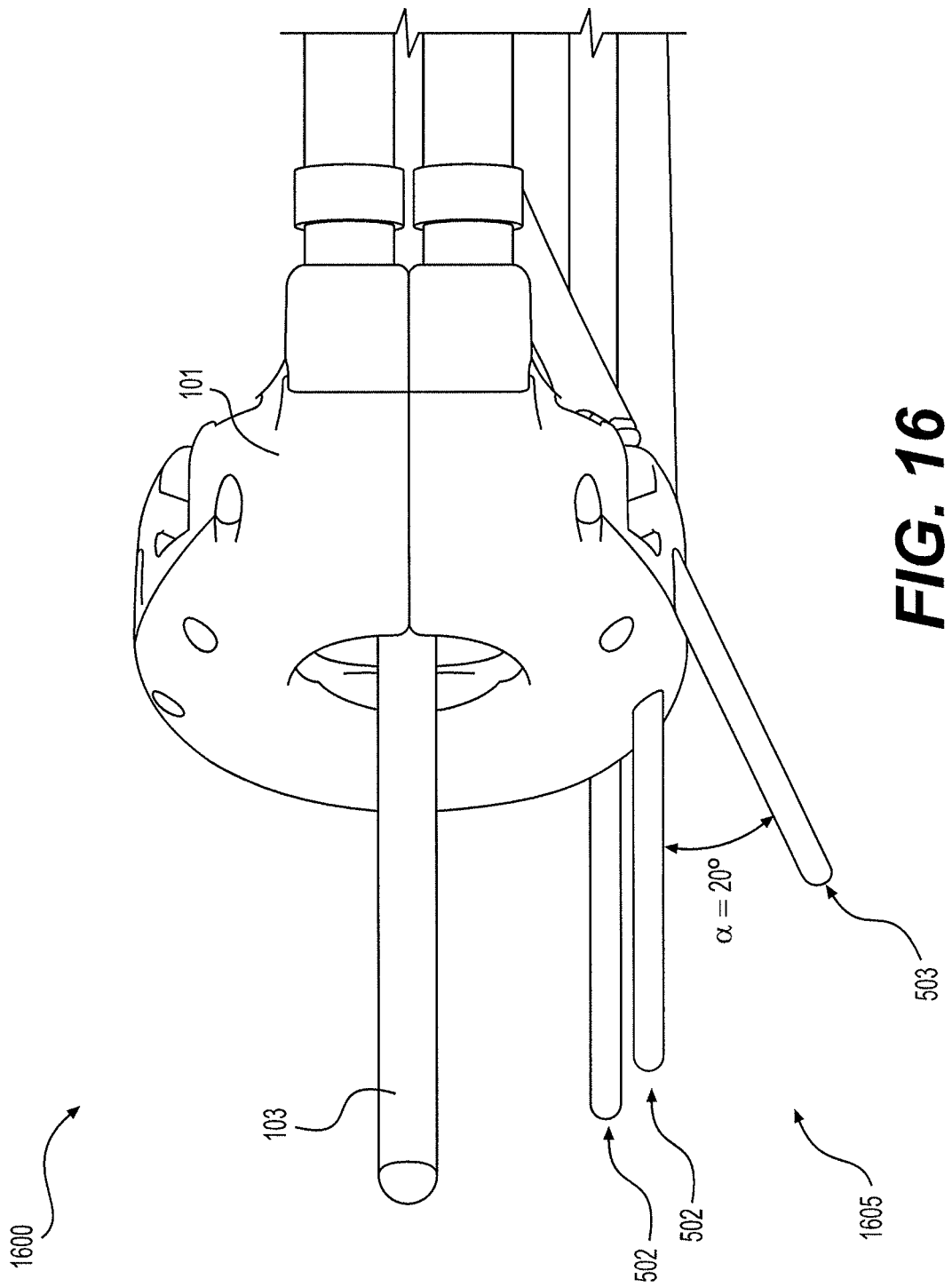
FIG. 16 illustrates an example ring-shaped ovoid applicator head assembly with interstitial needles, consistent with embodiments of the present disclosure.

FIG. 16 illustrates an example ring-shaped ovoid applicator head assembly 1600 with interstitial needles, consistent with embodiments of the present disclosure. In some embodiments, interstitial needles may be directed parallel to central applicator tube 103 by openings in ring-shaped ovoid applicator head pieces 101. In some embodiments, openings in ring-shaped ovoid applicator head pieces 101 may direct interstitial needles in an oblique angle offset from the direction of central applicator tube 103. For example, as shown in FIG. 16, oblique interstitial needle 503 is offset by 20 degrees (e.g., oblique offset angle 1605) from parallel interstitial needles 502. Additional offset angles may be used. In other embodiments, combinations of different offset angles may be used.

Figure 17:
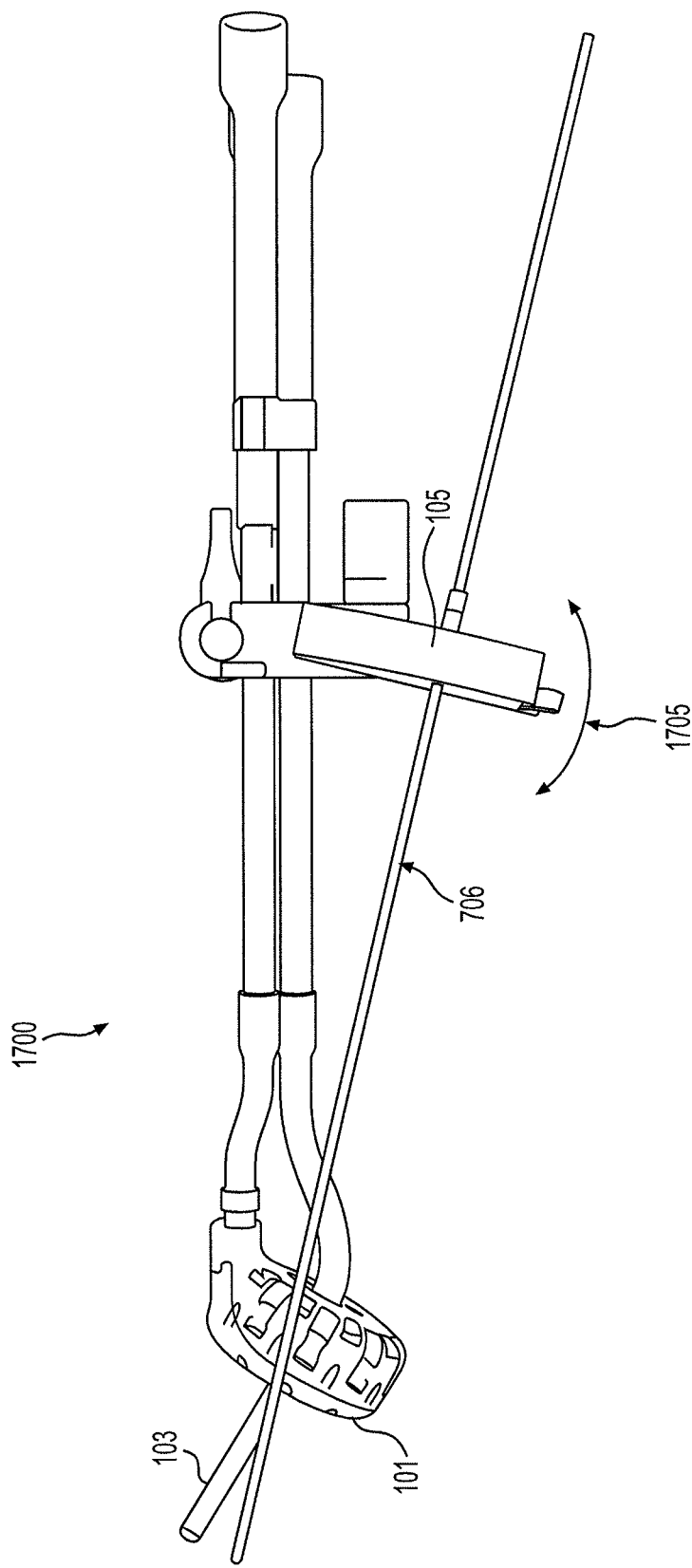
FIG. 17 illustrates an example ring-shaped ovoid applicator assembly with a perineal template, consistent with embodiments of the present disclosure.

FIG. 17 illustrates an example ring-shaped ovoid applicator assembly 1700 with a perineal template 105, consistent with embodiments of the present disclosure. In some embodiments, perineal template 105 may rotate about an axis to angle needle 706. For example, perineal connector 106 may facilitate template angle adjustment 1705 to direct metal needles to reach target areas. Additional angular adjustments may facilitate wider potential treatment areas consistent with this disclosure.

Figure 18:
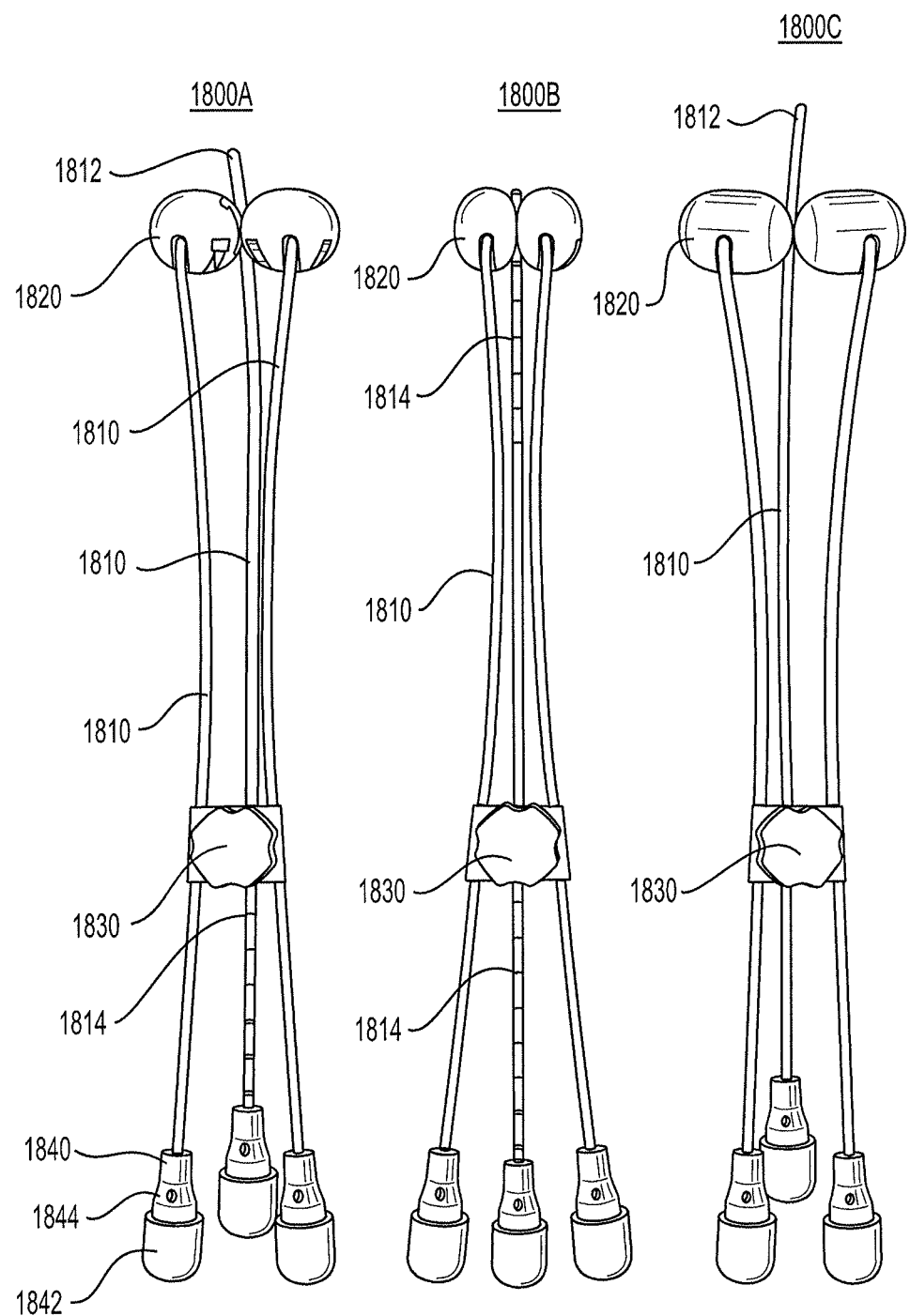
FIG. 18 illustrates example systems of ergonomic brachytherapy applicators, consistent with embodiments of the present disclosure.

FIG. 18 illustrates example systems of ergonomic brachytherapy applicators, consistent with embodiments of the present disclosure. FIG. 18 includes applicator 1800A, applicator 1800B, and applicator 1800C. Consistent labeling is used for the parts of each applicator. Multiple items may have the same labeling, while highly repetitive items may not all be labeled, such as applicator tubes 1810, for example.

Example applicator 1800A may include three applicator tubes 1810. Each applicator tube may be formed by a single tube of stiff material. In an embodiment, the applicator tubes 1810 may be bent. For example, in some embodiments, applicator tubes 1810 may be shaped to match the anatomical structure of a patient, which could increase patient comfort during usage. Further, anatomically shaped applicator tubes may be easier to use by the operating physician.

For instance, as depicted in applicator 1800A, applicator tubes 1810 bend towards the center halfway down the tube. This curvature may create a streamlined applicator that is more compact and easier to maneuver than other applicators. Having a single tube, rather than separate broken sections connected at joints, may ensure that the inner channel is free of kinks that may prevent smooth travel of radiation dosages.

Applicator tubes 1810 may be made of a gamma radiation resistant material. In an embodiment, applicator tubes 1810 may be made from a matrix material. For example, Polyphenylsulfone (PPSU), polyether ether ketone (PEEK), polyetherimide (PEI), ethylene tetrafluoroethylene (ETFE), polyamide-imide (PAI), polyimide (PI), polystyrene (PS), thermoplastic polyurethane (TPU), polysulfone (PSU), polyethersulfone (PES), and phenolics may be used to form applicator tubes 1810. In an embodiment, applicator tubes 1810 may be made in any shape with any plastic, including thermoharder, thermoplastic, and elastomer materials, using an autoclave process. The autoclave process may autoclave pre-impregnated wires, fibers, or mesh. Mesh may be wrapped along an inner tube, impregnated with synthetic material, and then a mold may apply pressure to shape the mesh, strengthening the material. In an embodiment, applicator tubes 1810 may be made using pulltrusion or pull-braiding techniques, extrusion with braiding and winding, dipping with braiding and winding, and spraying with braiding and winding. These techniques may apply a basecoat of material prior to winding and/or braiding fibers over the basecoat for reinforcement and increased structural integrity. A top coat of material may be added over the fibers to seal the outside surface of the applicator tubes.

Figure 19:
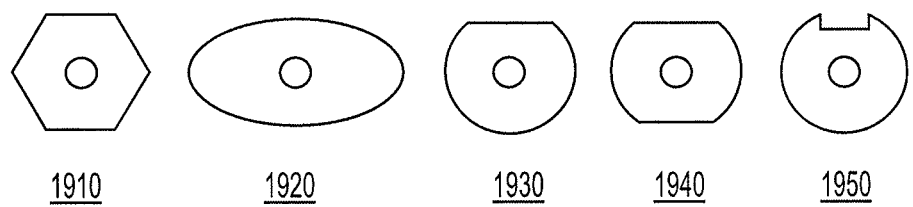
FIG. 19 illustrates diagrams of example applicator tubes with a cross-sectional view, consistent with embodiments of the present disclosure.

Applicator tubes 1810 may have a non-circular cross-section. FIG. 19 illustrates diagrams of example applicator tubes with a cross-sectional view, consistent with embodiments of the present disclosure. Example cross-section 1910 may include a hexagonal exterior cross-section. Example cross section 1920 may include an elliptical exterior cross-section. Example cross-section 1930 may include a circular cross-section with a flat section. Example cross-section 1940 may include a circular cross-section with two parallel flat sections. Example cross-section 1950 may include a circular cross-section with a notch channel. Because the cross-sections are not circular, they may be more easily secured, preventing rotation about the axis of the applicator tube. Having a flat face on the applicator tube may allow a securing mechanism to effectively apply force perpendicular to the flat section. Because stock circular tubes may be readily available, cross-sections that are closely related to circular cross-sections, such as Example cross-section 1930, may be useful. For example, example cross-section 1930 may be manufactured by modifying stock tubes with a circular cross-section. Example cross-section 1910 may benefit in being able to be secured at multiple angles, using different faces of the hexagonal cross-section. Example cross section 1920 may provide a tube with the advantage of having a continuous surface with no sharp edges. Each tube may have a circular inner channel that enables the source to move through the channel. For example, a radiation source, a dummy source, or a tracking device may move through the channel.

Figure 20:
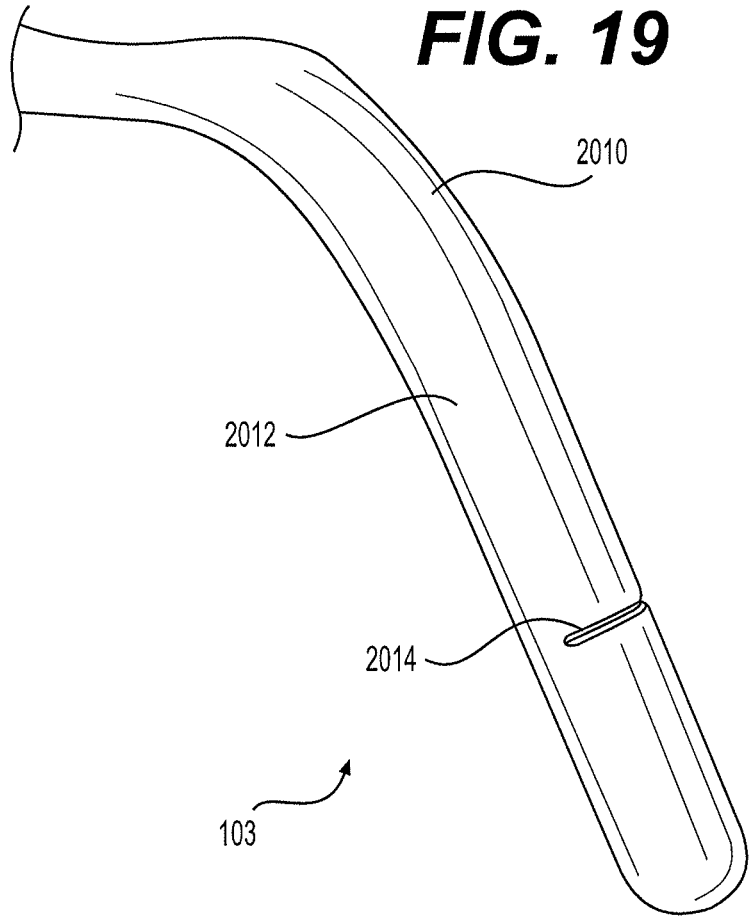
FIG. 20 illustrates an example ergonomic tube applicator, consistent with embodiments of the present disclosure.

Returning to FIG. 18, applicator tubes 1810 may have closed tube ends 1812 at one end. Tube ends 1812 may hold radiation sources for treatment. FIG. 20 illustrates an example ergonomic tube applicator end 2010, consistent with embodiments of the present disclosure.

Tube applicator end 2010 may transition from a circular cross-section to a non-circular cross-section having flat face 2012. The non-circular cross-section may have one flat face (e.g., example cross-section 1930 of FIG. 19) or two parallel flat faces (not shown; e.g., example cross-section 1940 of FIG. 19). As shown in FIG. 20, tube applicator end 2010 may have notch 2014 circumscribing an end section. Notch 2014 may be located at a predefined distance from the tip of tube applicator end 2010. While not depicted, multiple notches may be placed at pre-defined intervals. Flat face 2012 and notch 2014 may be used individually or in combination to secure applicator accessories to tube applicator end 2010.

Returning to FIG. 18, the two outer applicator tubes of applicator tubes 1810 for applicator 1800A may attach to ovoids 1820. Ovoids 1820 may be various shapes and size to provide effective treatment to a patient. In an embodiment, the shape of ovoids 1820 may be matched to the anatomical structure of the patient, increasing or decreasing in size to fit the patient. Ovoids 1820 may include shielding, which may attenuate or direct the radiation that may emanate from sources placed at the end of applicator tubes 1810. Ovoids 1820 may include holes for the placement of interstitial needles. Tube ends 1812 may extend beyond ovoids 1820. Thus, ovoids 1820 may mark how far a center applicator tube may need to extend to the treatment site. For example, in example applicator 1800B, tube end 1812 may not extend beyond ovoids 1820. For applicator 1800C, tube end 1812 may extend far beyond ovoids 1820. Example applicator 1800A may include tube end 1812 that extends a medium distance. Tube markings 1814 may mark applicator tubes 1810 at regular intervals, allowing a physician to measure the distance at which an applicator tube tip extends.

Applicator tubes 1810 may be secured using tube clamps 1830. In an embodiment, tube clamps 1830 may prevent the sliding or rotation of applicator tubes 1810. For example, tube clamps may include a screw or other mechanism to apply force to a side of applicator tubes having a non-circular cross-section.

Applicator tubes 1810 may include ports 1840 that may each receive units, such as radiation sources, dummy sources, or tracking devices. For example, a physician may insert a radiation source and use a needle or cannula to move a radiation source into a treatment position. Ports may be covered before, during, or after use. For example, ports 1840 may be covered by port caps 1842 when not in use. Port caps 1842 may block debris from entering applicator tubes 1810. Ports 1840 may identify which treatment site the port corresponds to. In an embodiment port labels 1844 include may include a symbol or other identification mechanism conveying the location of the end tube. For example, port labels 1844 may numerically label ports 1840. In other examples, port labels 1844 include a description, such as "center tube" or "left ovoid tube." Other labels may use additional combinations of numbers, letters, and/or symbols.

FIG. 21 illustrates an alternatively shaped applicator assembly 2100. Assembly 2100 depicts applicator head pieces 2101 that are not ring-shaped. Instead, head pieces 2101 may be square-shaped with rounded corners, as shown. While head pieces 2101 are depicted with a certain shape, additional designs may utilize further shape variations without pointed edges, such as ovals or a teardrop shape, for example. Regardless of shape, head pieces 2101 may have an opening in the center between the two head pieces 2101 to host central applicator tube 103.

As shown, head pieces 2101 may be integrated into source delivery tubes. For example, as shown in FIG. 21, each head piece 2101 may include an integrated channel 2102. Integrated channel 2102 may connect direct to source tubes to receive radiation sources. Additional channel designs may be used in headpieces 2101 to achieve desired radiation patterns. For example, channel 2102 may curve or extend to allow radiation sources to be located proximate to tumors.

Figure 22A:
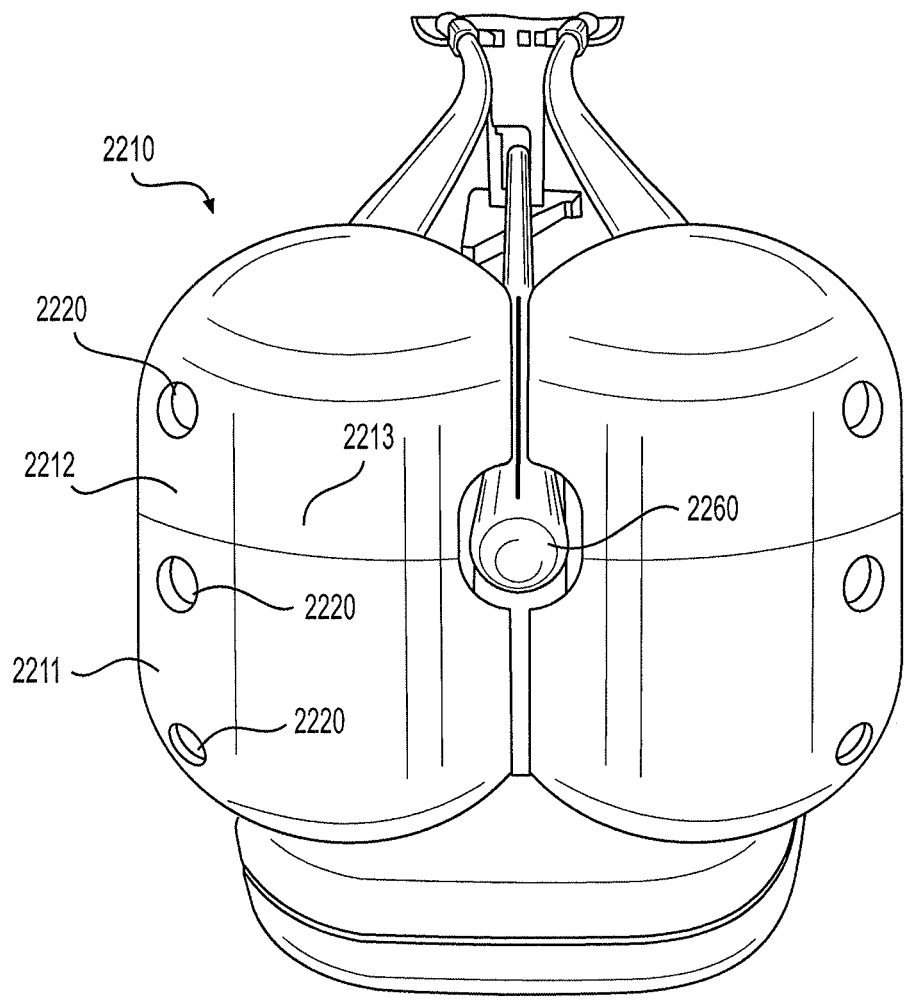
Figure 22B:
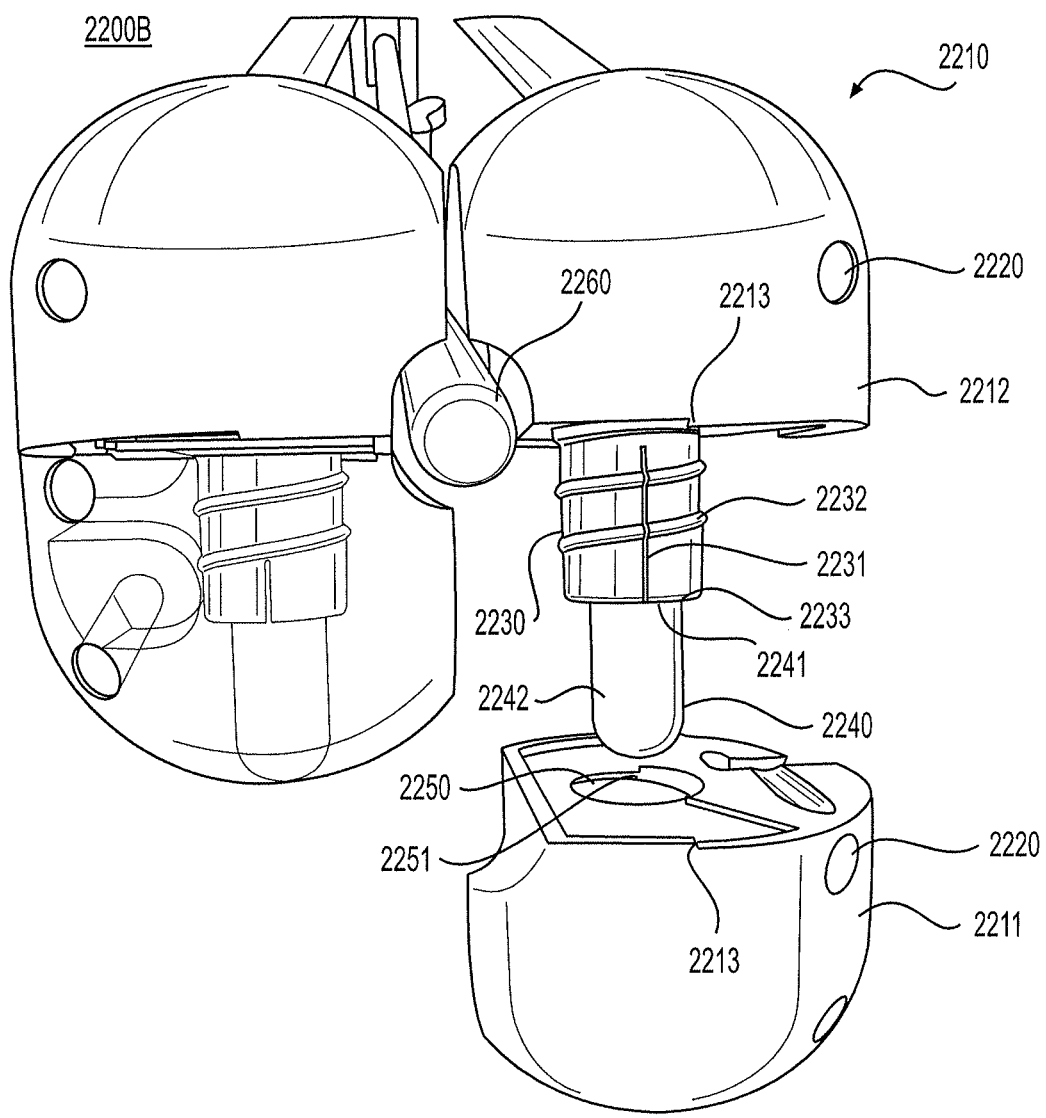
Figure 22C:
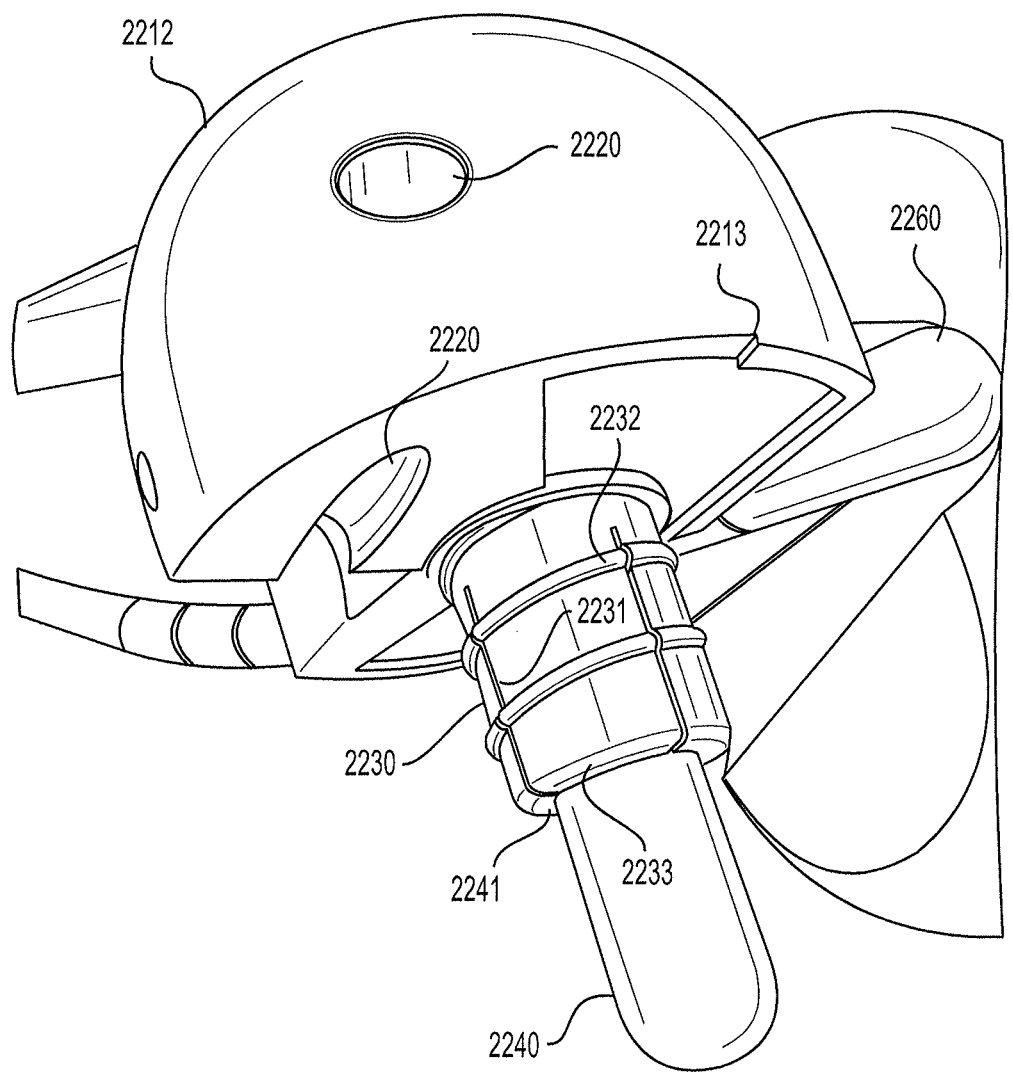
Figure 22E:
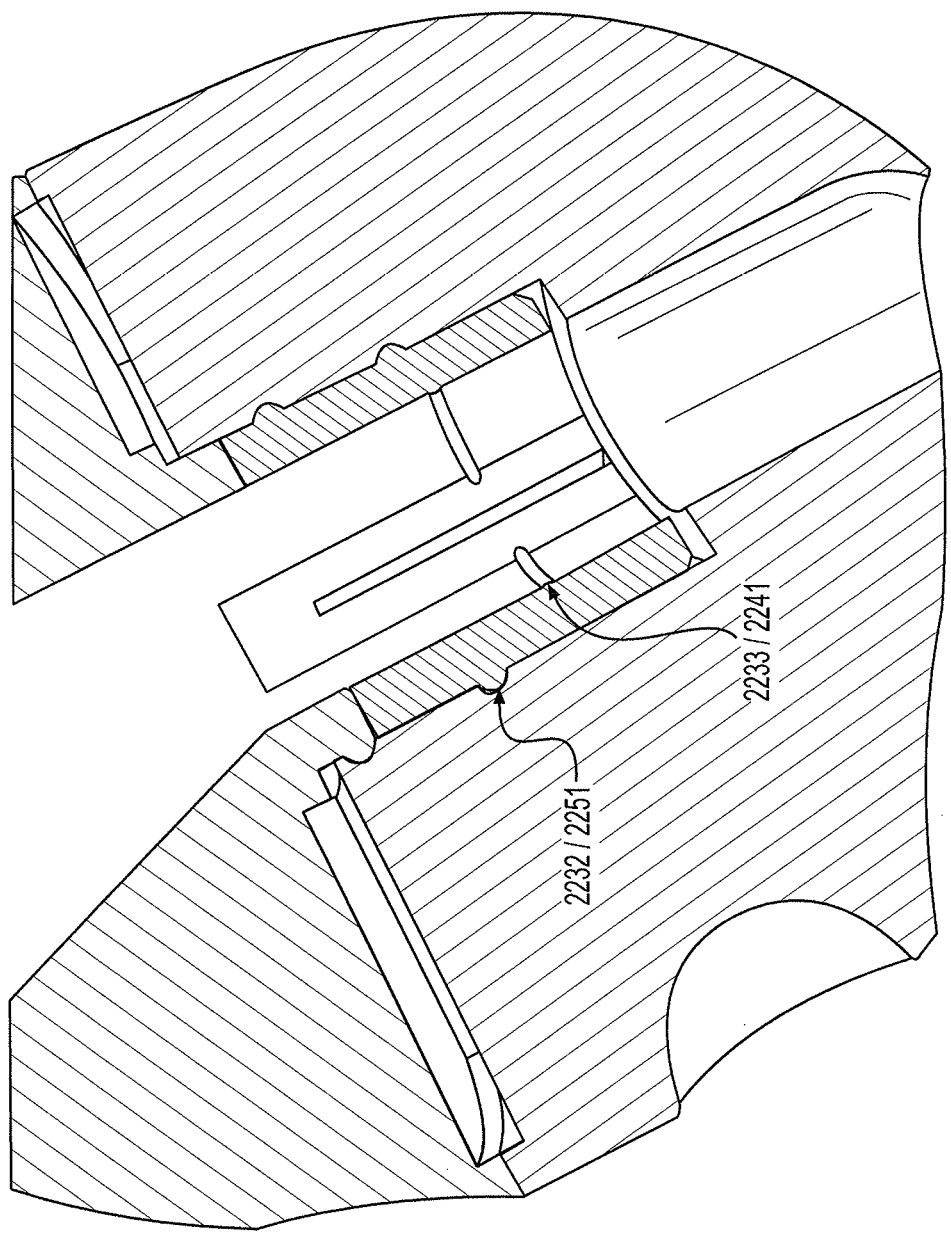
Figure 22F:
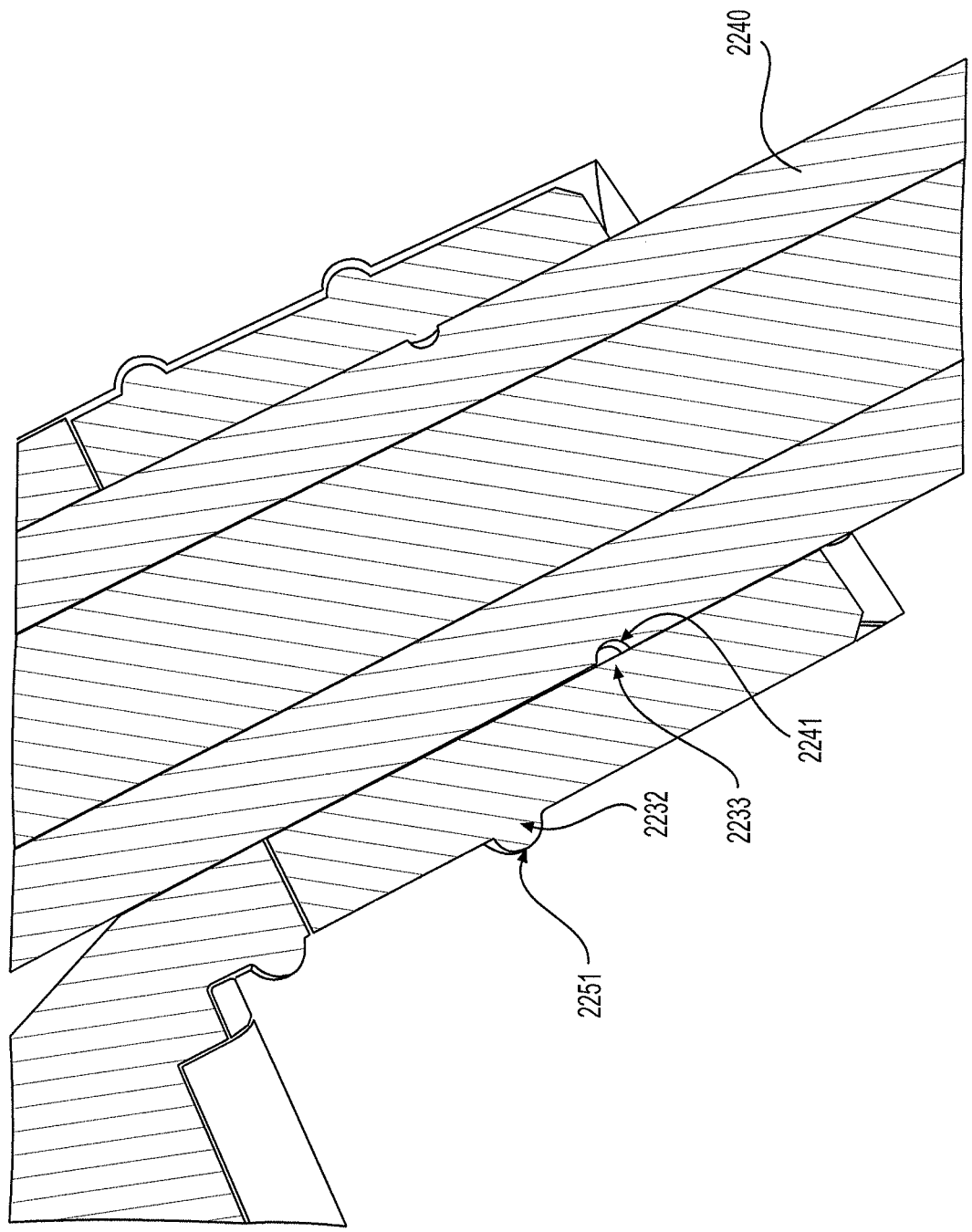

FIGS. 22A, 22B, 22C, 22D, 22E, and 22F illustrate an example applicator assembly including an ergonomic ovoid, consistent with embodiments of the present disclosure. FIG. 22A may illustrate complete assembly 2200A, while FIG. 22B illustrates an expanded view an example applicator assembly 2200B and FIG. 22C illustrates a magnified view of partially assembled applicator assembly 2200C, consistent with embodiments of the present disclosure. FIGS. 22D, 22E, and 22F include additional cross-sectional views of an example applicator assembly.

Complete assembly 2200A may include ovoid 2210, which is may be made up of upper portion 2212 and lower portion 2211. When assembled ovoid 2210 may be shaped to have an opening for intra uterine tube 2260. Ovoid 2210 may secure intra uterine tube 2260. For example, ovoid 2210 may be shaped to engage with intra uterine tube 2260 when ovoid 2210 is assembled. When assembled, ovoid 2210 may have multiple sites 2220 which guide interstitial needles.

Upper portion 2212 and lower portion 2211 connect using a screw mechanism. As shown in example applicator assembly 2200B of FIG. 22B, upper portion 2212 includes integrated screw 2230. The screw allows upper portion 2212 to connect to lower portion 2211 and secure ovoid 2210 to intra uterine tube tip 2240. Integrated screw 2230 may be hollow to have room to receive intra uterine tube tip 2240. Integrated screw may engage with opening 2250 of lower portion 2211. For example, integrated screw 2230 may have helical ridge 2232 which may slide along channel 2251 of opening 2250.

In order to secure ovoid 2210 to intra uterine tube tip 2240, integrated screw may have spacer 2231 which allows the walls of integrated screw 2230 to expand and contract relative to the center axis of integrated screw 2230. Ovoid 2210 may be designed to prevent damage to ovoid 2210 or intra uterine tube tip 2240 caused by over-rotation or over-torqueing integrated screw 2230. In an embodiment, upper portion 2212 and lower portion 2211 may each have notches 2213 which prevent the over-rotation. When integrated screw 2230 is sufficiently engaged with opening 2250, notches 2213 may meet, indicating the desired amount of rotation for integrated screw 2230.

Intra uterine tube tip 2240 may be shaped to secure to ovoid 2210. In an embodiment, intra uterine tube tip 2240 may have notch 2241 to engage with ridge 2233 on the end of the opening of integrated screw 2230. For example, opening 2250 may have slightly tapered sides, such that, as helical ridge 2232 travels along channel 2251 deeper into opening 2250, the circumference of opening decreases with depth. The space of spacer 2231 may decrease, which may tighten integrated screw around intra uterine tube tip 2240. Intra uterine tube tip 2240 may also be shaped to prevent rotation of upper portion 2212. For example, intra uterine tube tip 2240 may have flat face 2242, creating a non-circular cross-section. The opening of integrated screw 2230 may have a similar non-circular cross-section to axially fix upper portion 2212.

Upper portion 2212 and lower portion 2211 may be manufactured as single pieces. In an embodiment, integrated screw 2230 may be molded into the body of upper portion 2212. Likewise, opening 2250 may be molded into lower portion 2211. Upper portion 2212 and lower portion 2211 may be made out of similar materials as applicator tubes. In an embodiment ovoid 2210 is made using a polymer. For example, upper portion 2212 and lower portion 2211 may be made using an injection molded process and/or machining.

Ovoid 2210 may include integrated shielding to prevent radiation from emitting outside of target treatment area. For example, ovoid 2210 may include different materials internally or externally that may block radiation. The materials may be strategically placed based on the target treatment location.

Figure 23:
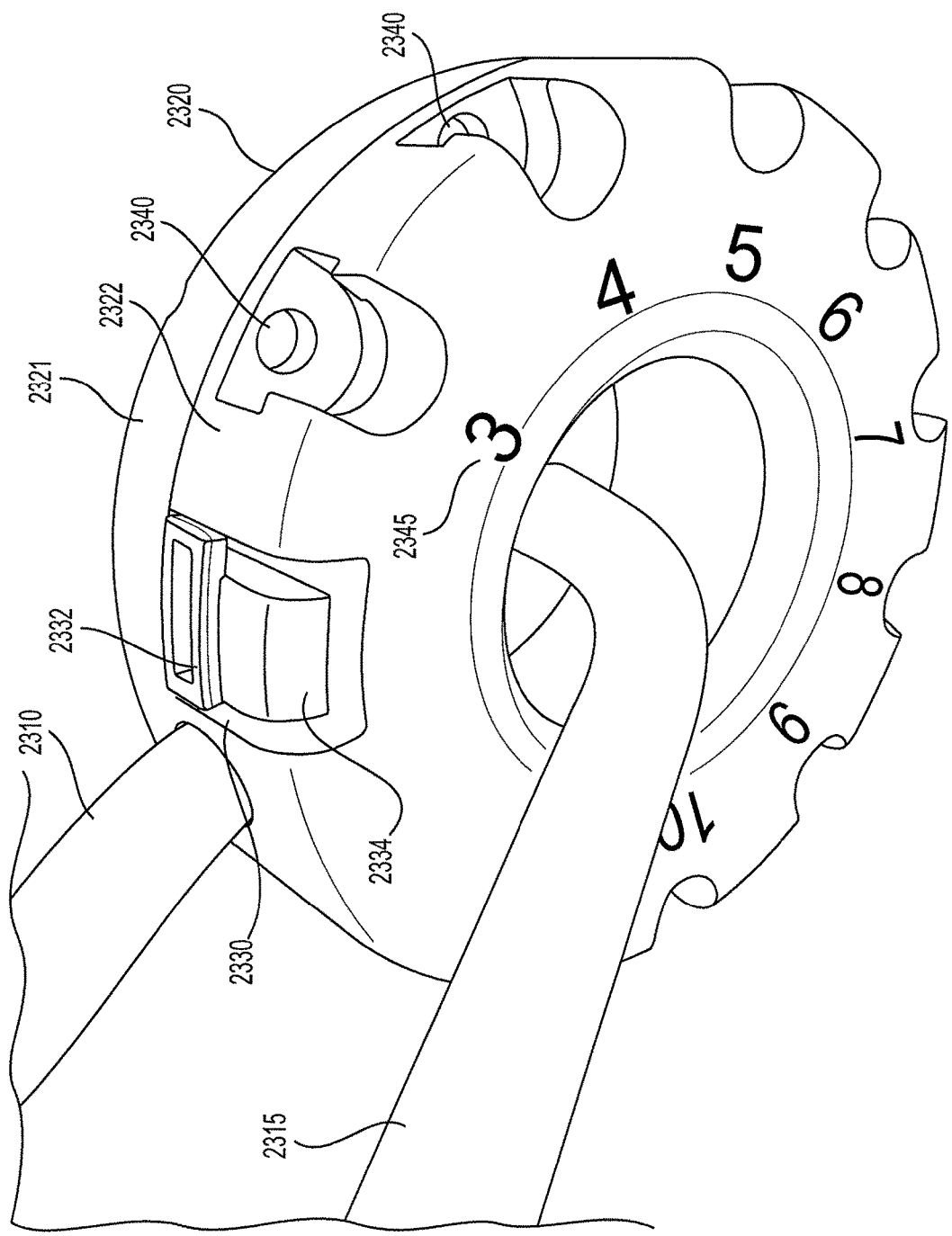
FIG. 23 illustrates an example applicator assembly including ring caps, consistent with embodiments of the present disclosure.

FIG. 23 illustrates an example applicator assembly 2300 including ring applicator 2320, consistent with embodiments of the present disclosure. Ring applicator 2320 may enclose ring tube 2310. Intra uterine tube 2315 may be mounted together with ring tube 2310 and extend through the opening of ring applicator 2320. In an embodiment, ring applicator 2320 may include two separate parts, or ring caps, which align to envelop ring tube 2310. For example, ring applicator may have upper ring cap 2321 and lower ring cap 2322.

Upper ring cap 2321 and lower ring cap 2322 may be secured together using a tool-free close mechanism. In an embodiment, click tab 2330 may connect upper ring cap 2321 and lower ring cap 2322. For example, tab 2334 of click tab 2330 may engage gate 2332. ring applicator 2320, including click tab 2330, may be made of an elastic material. For example, tab 2334 may flex without the use of tools to disengage click tab 2330, separating upper portion (e.g., upper ring cap 2321) and lower portion (e.g., lower ring cap 2322), and freeing ring tube 2310 from ring applicator 2320. This may be advantageous for easy assembly and streamlined sterilization processes.

Ring applicator 2320 may have sites 2340 for guiding interstitial needles. Sites 2340 may be labeled using numbers, characters, or symbols. For example, labels 2345 may indicate the location of sites 2340. The sites may include geometry to secure tube ends which may carry interstitial needles. For example, sites 2340 may be shaped to include brackets, which may engage tube ends to secure the tube ends via a shape-controlled fit or a friction fit. In an embodiment, sites 2340 may be located in varying patterns. For example, sites 2340 may form multiple rows, or a honeycomb pattern. The location of sites 2340 may be customized based on a treatment plan, patient anatomy, or a location of a tumor. In an embodiment, sites 2340 may orient the tube ends, and hence, the interstitial needles in specific directions. For example, sites 2340 may include tube mounting points that are angled. The angles may be advantageous to route interstitial needles around anatomical structures (e.g., organs) and accommodate better and/or further reach target regions. Sites 2340 may have different angles. For example, sites 2340 may include tube mounting points that are specifically angled to orient needles to match a particular treatment plan, patient anatomy, or tumor location. Tube mounting points may be customized to orient needles as need for treating a particular patient. Sites 2340 may be located and oriented in any direction necessary for treatment without limitation.

Figure 24:
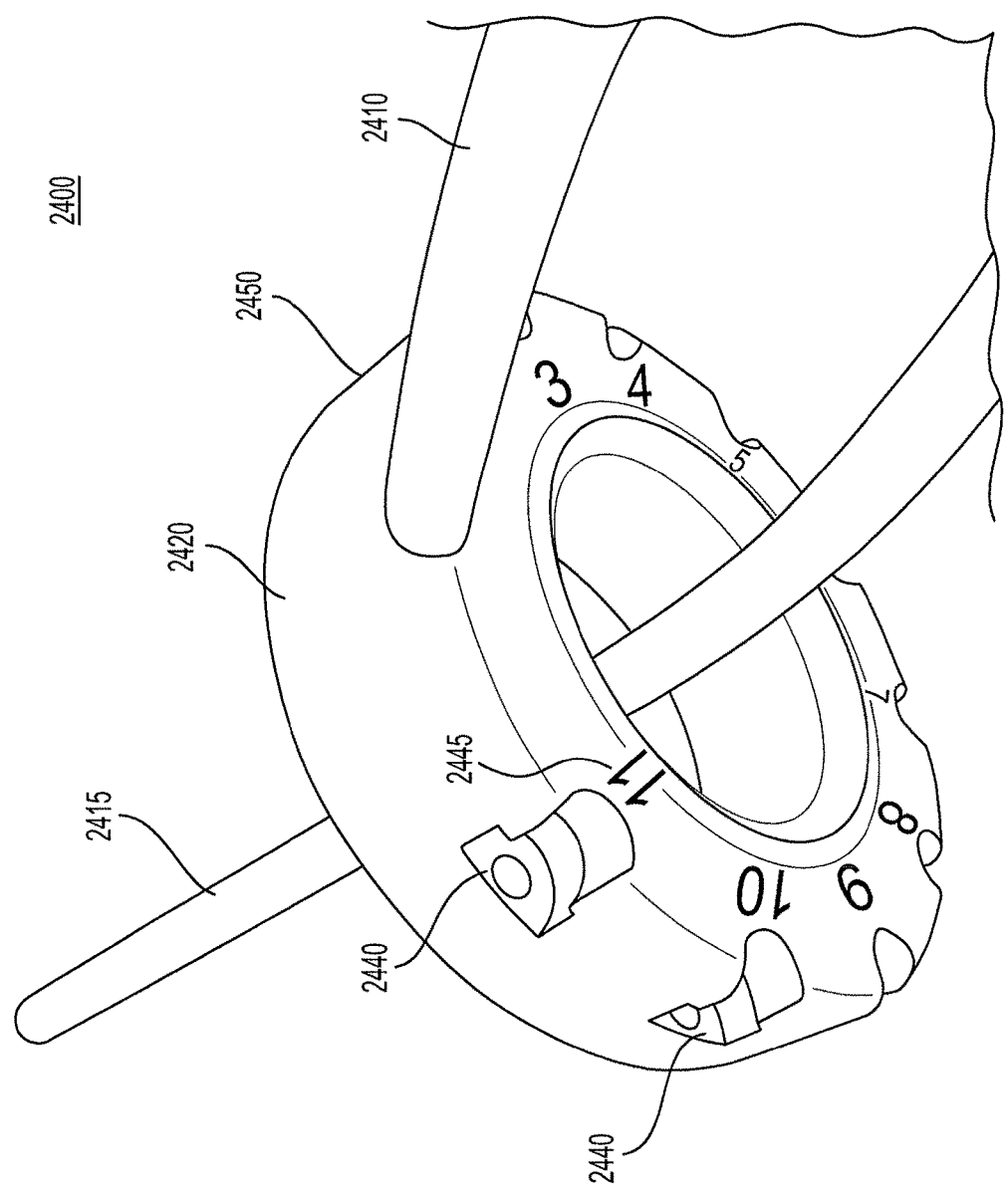
FIG. 24 illustrates another example applicator assembly including another ring applicator, consistent with embodiments of the present disclosure.

FIG. 24 illustrates another example applicator assembly 2400 including ovoid ring 2420, consistent with embodiments of the present disclosure. Ovoid ring 2420 may enclose circular applicator 2410. Intra uterine applicator 2415 may be mounted together with circular applicator 2410 and extend through the opening of ovoid ring 2420. In an embodiment, ovoid ring 2420 may envelop circular applicator 2410. For example, ovoid ring may be permanently molded around circular applicator 2410 during the manufacturing process. By sealing circular applicator, the sterilization process may be streamlined by eliminating the number of separate parts. Further, because no assembly is required for ovoid ring 2420, physicians may operate more efficiently.

Ovoid ring 2420 may have sites 2440 for guiding interstitial needles. Sites 2440 may be labeled using numbers, characters, or symbols. For example, labels 2445 may indicate the location of sites 2440.

Figure 25A:
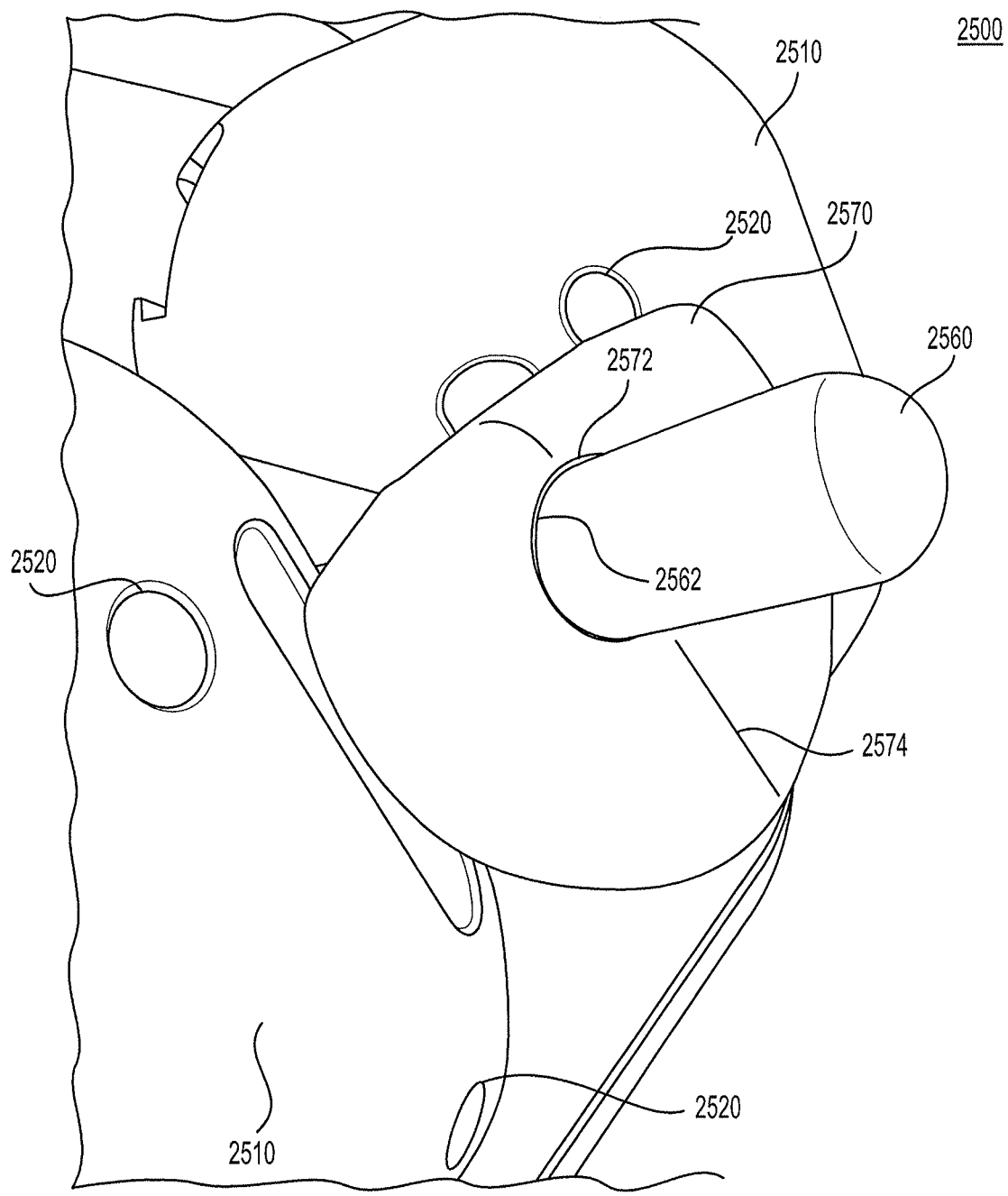
FIGS. 25A and 25B illustrate an example applicator assembly including a cervical stopper, consistent with embodiments of the present disclosure.
Figure 25B:
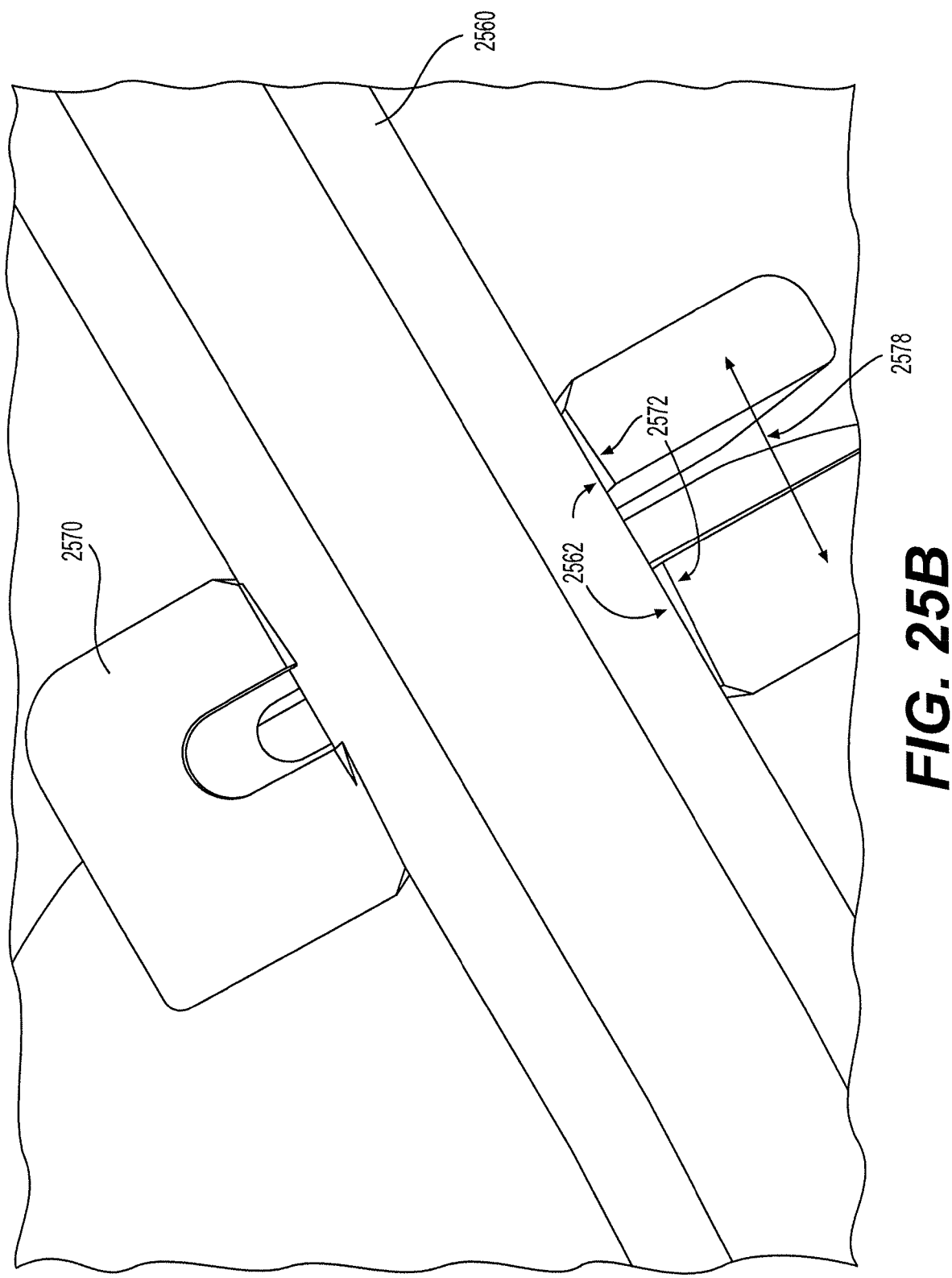

FIGS. 25A and 25B illustrate an example applicator assembly 2500 including cervical stopper 2570, consistent with embodiments of the present disclosure. Cervical stopper may attach to intra uterine tube tip 2560. In an embodiment, cervical stopper 2570 may engage with intra uterine tube tip 2560 to securely attach. For example, cervical stopper may have elastic opening 2572, which may expand and compress due to the polymer material of cervical stopper 2570. Opening 2572 may engage with notch 2562 in intra uterine tube tip 2560. By engaging with notch 2562, cervical stopper may not travel along the axis of intra uterine tube tip 2560. In some embodiments, cervical stopper 2570 may utilize a tool-free design. For example, as shown in FIG. 25B, tension in opposing sides of cervical stopper 2570 may create force 2578 that pushes elastic opening 2572 against one or more notches 2562. A user need may thus only apply a compression force (e.g., by squeezing opposing sides) to freely move cervical stopper 2570 (e.g., to slide along intra uterine tube tip 2560 or remove completely). Additionally, intra uterine tube tip 2560 may have a non-circular cross-section to prevent rotation of cervical stopper 2570 about the axis of intra uterine tube tip 2560.

Cervical stopper may be annotated. In an embodiment, cervical stopper 2570 may have labeling to assist physicians in assembly and operation of cervical stopper 2570. For example, cervical stopper 2570 may have center line 2574 drawn, indicating the center of intra uterine tube tip 2560.

As depicted in FIG. 25A, cervical stopper 2570 may be used with ovoids 2510, which may have sites 2520 for interstitial needles. In other embodiments, cervical stopper 2570 may be used with other ovoid attachments or without ovoids.

Figure 26A:
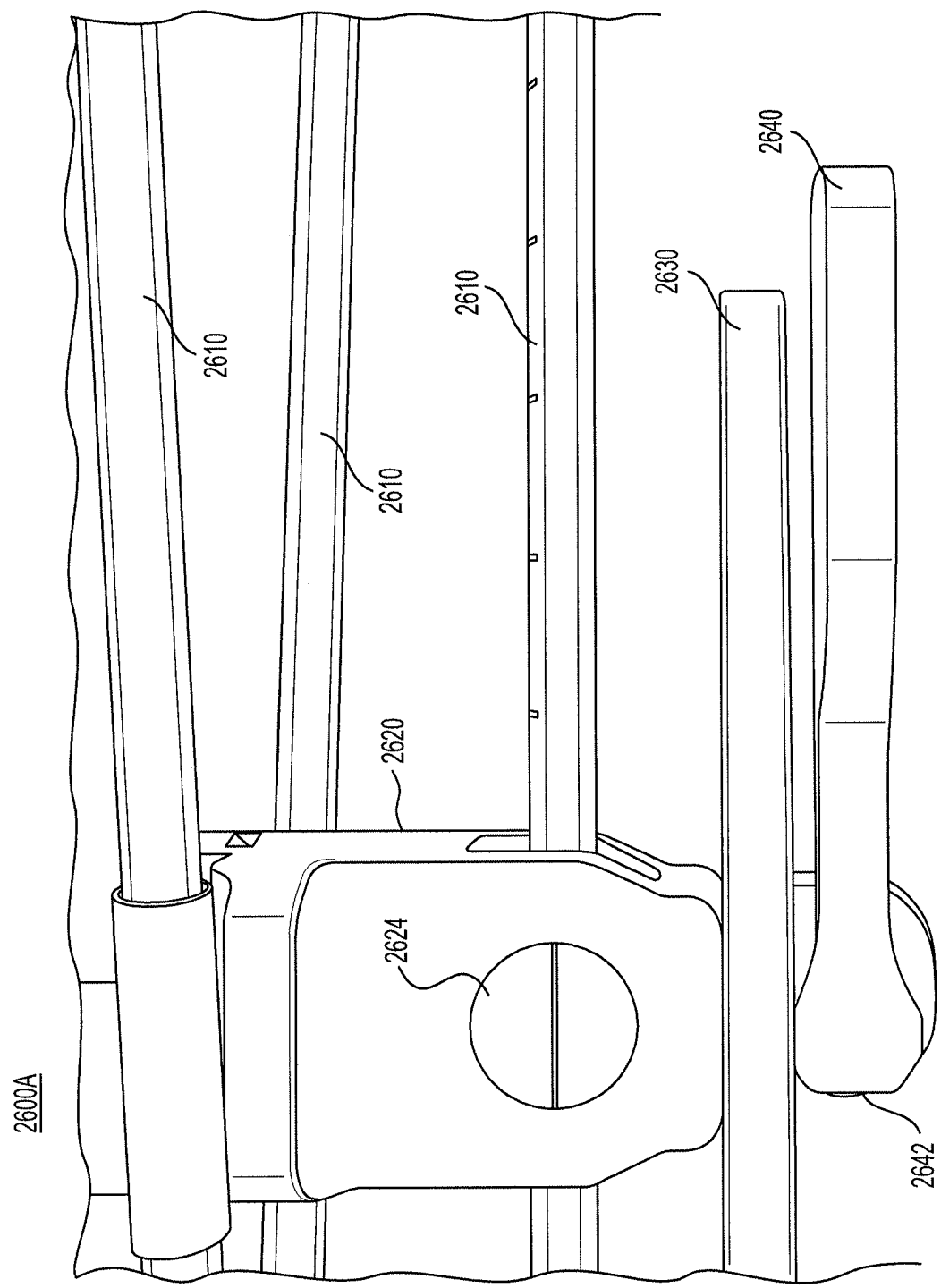
FIGS. 26A, 26B, and 26C illustrate an example applicator including a rectal retractor, consistent with embodiments of the present disclosure.
Figure 26B:
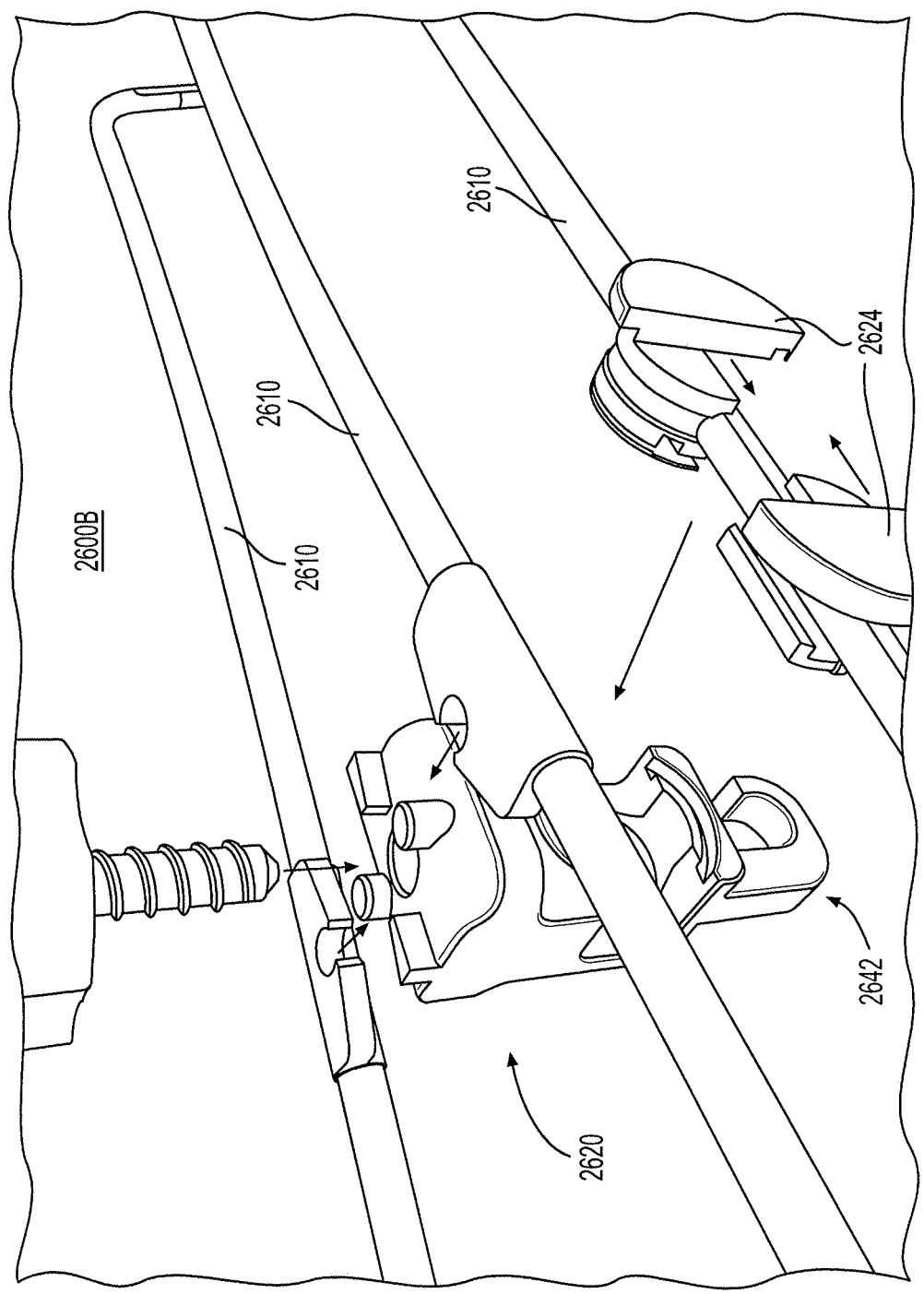
Figure 26C:
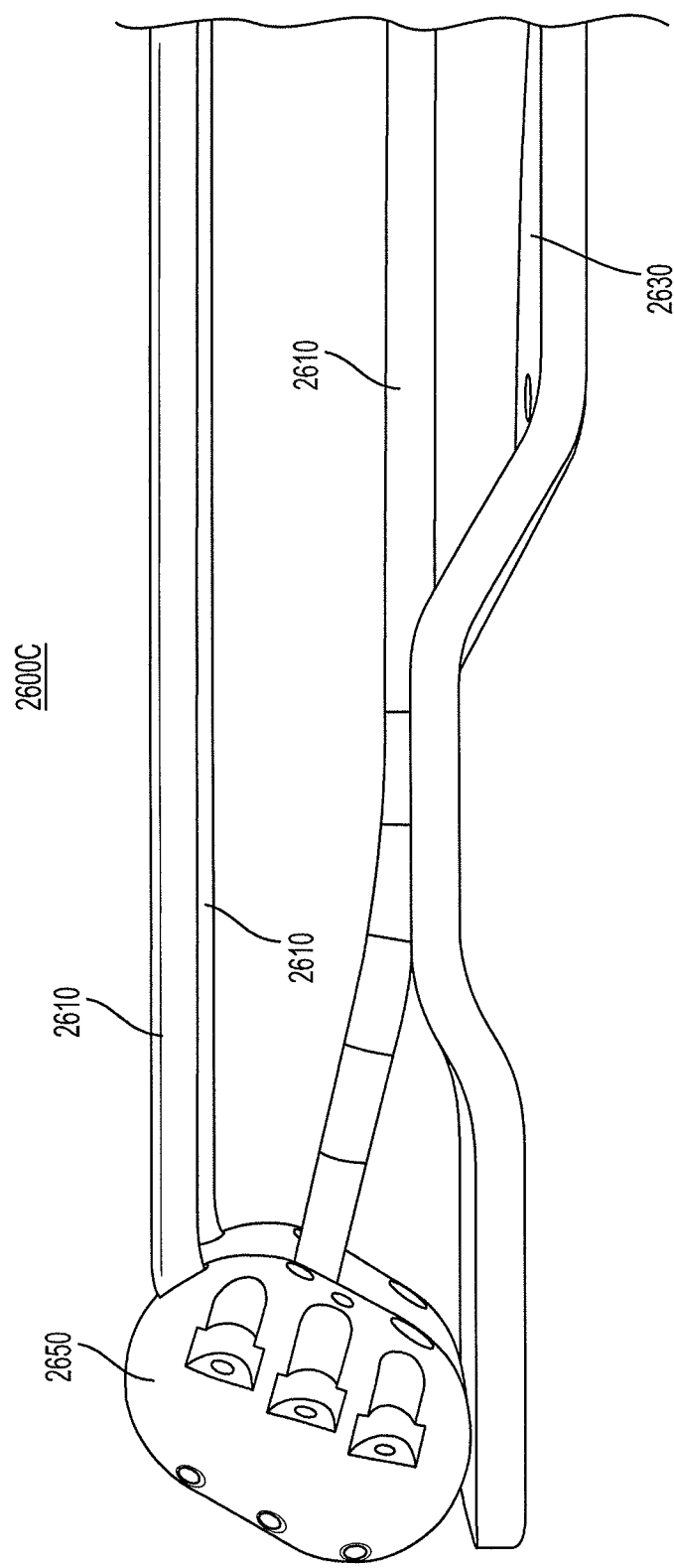

FIGS. 26A, 26B, and 26C illustrate an example applicator including a rectal retractor including control portion 2600A and applicator end 2600B, consistent with embodiments of the present disclosure.

In an embodiment, clamp 2620 may secure applicator tubes 2610 at an anchor point, holding the tubes together. For example, clamp 2620 may use screw 2624 to fix the location of tubes 2610 using a friction fitting or shape-defined fitting. Claim 2620 may then move all applicator tubes 2610 at once. For example, tubes 2610 secured by clamp 2620 may move forwards and backwards as a single unit.

In an embodiment, clamp 2620 may be secured to paddle 2630. For example, clamp 2620 may selectively slide along paddle 2630. Lever 2640 may include end portion 2642 to engage paddle 2630 and clamp 2620 using a friction fit or shape-defined fit. For example, when lever 2640 is parallel to paddle 2630, end portion 2642 may be wider, engaging paddle 2630. However, when lever 2640 is rotated to be perpendicular to paddle 2630, end portion 2642 may be less wide, removing the force holding paddle 2630 to clamp 2620. Paddle 2630, lever 2640, and end portion 2642 may be designed so that different lever positions may secure the location of clamp 2620 and tubes 2610. For example, lever 2640 may be designed so that end portion 2642 applies a force against paddle 2630 when lever 2640 is perpendicular to paddle 2630, which forms, for example a tool-free friction fit between paddle 2630 and end portion 2642.

When aligned to disengage, paddle 2630 may slide parallel to applicator tubes 2610. For example, during an operation, paddle 2630 may align with ovoids 2650, pressing against the patient. The physician may move paddle 2630 to an engaged position and may secure the location of clamp 2620 (and connected tubes 2610) for treatment using lever 2640. However, after treatment, a physician may move lever 2640 so that paddle 2630 may be moved to be disengaged, allowing a physician to use the paddle as leverage to apply force moving ovoids 2650 and any treatment parts away from the patient.

Figure 27:
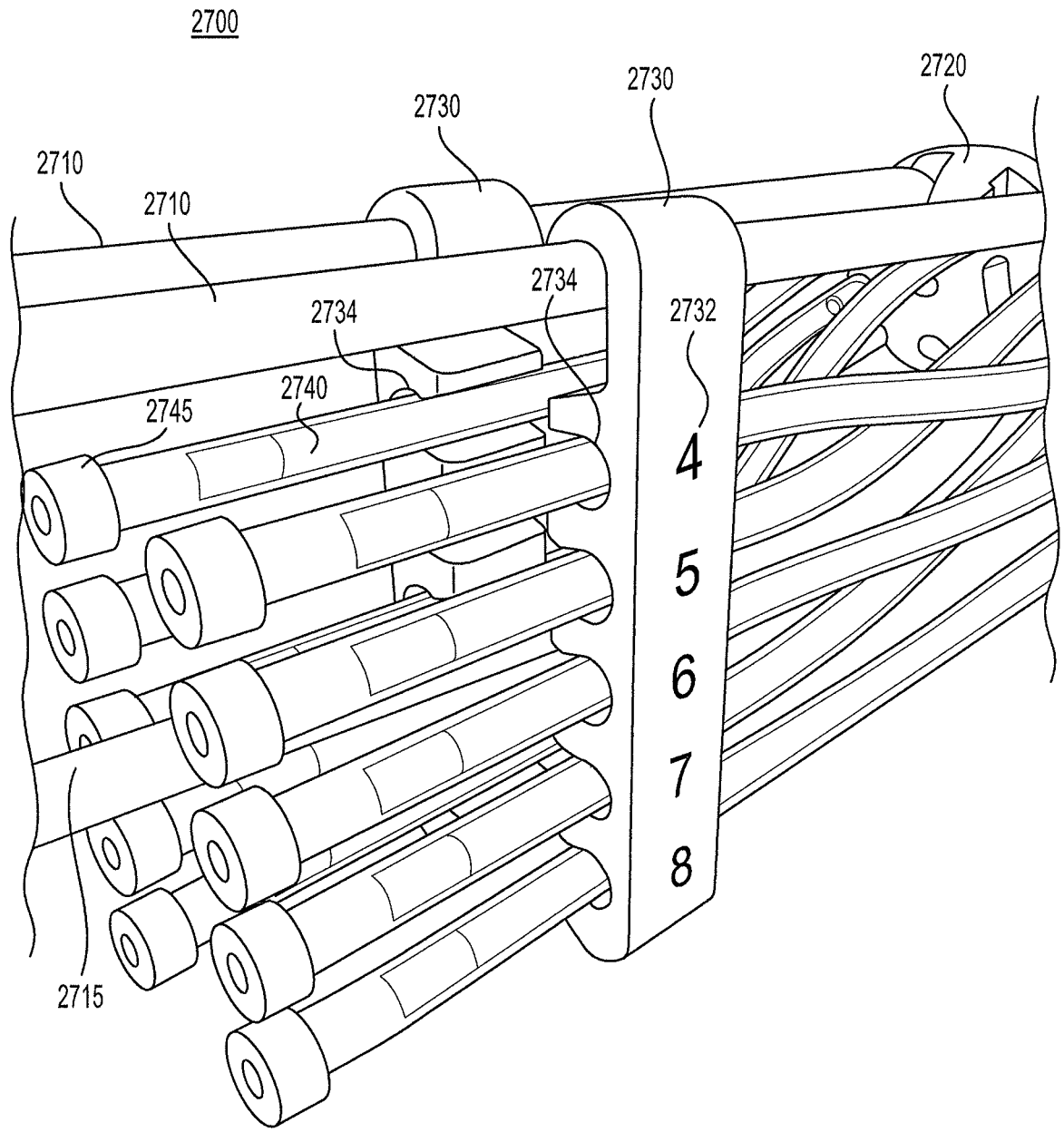
FIG. 27 illustrates an example applicator including a tube holding bracket, consistent with embodiments of the present disclosure.

FIG. 27 illustrates an example applicator 2700 including tube holding brackets 2730 (e.g., an example of bracelet 111), consistent with embodiments of the present disclosure. To apply interstitial needles to the sites on ovoids 2720, flexible tubes 2740 may have openings 2745 which receive interstitial needles. Further, flexible tubes 2740 may be used to guide the interstitial needles and radiation sources. When many needles are used many tubes are necessary. The tubes may be fixed to tube holding brackets 2730.

In an embodiment, tube holding brackets 2730 include tool-free securing mechanisms to hold flexible tubes 2740. For example, tube holding brackets 2730 may include individual brackets 2734 which may hold flexible tubes 2740 using a shape fit, snap fit, or friction fit. Physicians may press flexible tubes 2740 into individual brackets 2734 during operation to organize flexible tubes 2740. For example, tubes 2740 may be slightly wider than individual brackets 2734, allowing tubes 2740 to flex and squeeze into individual brackets 2734. The shape of tubes 2740 may secure and/or fixate their location using tube holding brackets 2730.

Individual brackets 2734 may be labeled using numbers, characters, or symbols. For example, labels 2732 may indicate the connection location of a tube secured in a given individual bracket.

In this disclosure, various embodiments have been described with reference to the accompanying drawings and embodiments. It will, however, be evident that various modifications and changes may be made thereto, and additional embodiments may be implemented, without departing from the present disclosure. The specification and drawings are accordingly to be regarded in an illustrative rather than restrictive sense.

For example, advantageous results may still be achieved if steps of the disclosed methods were performed in a different order and/or if components in the disclosed systems were combined in a different manner and/or replaced or supplemented by other components. Other implementations are also within the scope of the present disclosure.

It is to be understood that the foregoing general description are exemplary and explanatory only, and are not restrictive. Further, the accompanying drawings, which are incorporated in and constitute a part of this specification, illustrate embodiments of the present disclosure and together with the description, and are similarly not restrictive.

What is claimed is:

1. A brachytherapy applicator comprising:
   two applicator tubes configured to receive radiation sources, each applicator tube having a matching curved end section, the curved end sections of the applicator tubes combining to form a ring-shaped applicator having a middle opening;
   a central applicator tube configured to receive a radiation source that is located within the middle opening;
   a securing mechanism configured to receive and secure the applicator tubes to the central applicator tube;
   a locking mechanism configured to receive and secure the central applicator tube to the curved end sections; and
   a vaginal cap configured to connect to the applicator tubes, the vaginal cap including needle guides that align with needle openings of the applicator tubes.

2. The brachytherapy applicator of claim 1, the ring-shaped applicator further including a plurality of needle openings to guide interstitial needles, wherein a first subset of the plurality of needle openings is configured to direct interstitial needles at an angle offset from a direction of the central applicator tube.

3. The brachytherapy applicator of claim 2, further including a second subset of the plurality of needle openings to guide interstitial needles that is parallel to the direction of the central applicator tube.

4. The brachytherapy applicator of claim 3, wherein the plurality of needle openings alternate between being parallel to the direction of the central applicator tube and being at the angle offset from the direction of the central applicator tube.

5. The brachytherapy applicator of claim 1, wherein the vaginal cap is configured to connect to the applicator tubes using
   a tool-free connection.

6. The brachytherapy applicator of claim 1, further comprising a template for securing interstitial needles.

7. The brachytherapy applicator of claim 1, wherein the ring-shaped applicator has an outer diameter of 20 to 55 millimeters.

8. The brachytherapy applicator of claim 1, wherein the securing mechanism comprises a tool-free connector.

9. A brachytherapy applicator assembly comprising:
   two applicator tubes configured to receive radiation sources, each tube having a matching curved end section, the curved end sections of the applicator tubes combining to form a ring-shaped applicator having a middle opening and comprising a plurality of needle openings to guide interstitial needles;
   a central applicator tube configured to receive a radiation source that is located within the middle opening;
   a vaginal cap configured to connect to the applicator tubes, the vaginal cap including needle guides that align with the needle openings of the applicator tubes;
   a one-piece template for securing interstitial needles; and
   a tool-free connector to secure the applicator tubes to the central applicator tube.

10. The brachytherapy applicator assembly of claim 9, further comprising:
    a plurality of guiding tubes each connected to a different one of the needle guides of the vaginal cap.

11. The brachytherapy applicator assembly of claim 10, further comprising:
    an identification tag attached to each of the plurality of guiding tubes or needles including an indication of where the guiding tube leads or identifying the needle itself, respectively.

12. The brachytherapy applicator assembly of claim 10, further comprising:
    a bracelet comprising a plurality of tool-free brackets configured to secure the plurality of guiding tubes or needles.

13. The brachytherapy applicator assembly of claim 9, further comprising:
    a perineal template comprising a grid of perineal needle securing openings secured to the tool-free connector using a tool-free locking screw.

14. The brachytherapy applicator assembly of claim 9, wherein the vaginal cap comprises shielding configured to reduce radiation directed to a patient's rectum.

15. The brachytherapy applicator of claim 9, further including a first subset of the plurality of needle openings to guide interstitial needles at an angle offset from a direction of the central applicator tube.

16. The brachytherapy applicator of claim 15, wherein the angle offset from the direction of the central applicator tube is a 5 to 45 degree angle.

17. The brachytherapy applicator of claim 15, further including a second subset of the plurality of needle openings to guide interstitial needles parallel to the direction of the central applicator tube.

18. The brachytherapy applicator of claim 17, wherein the plurality of needle openings alternate between being parallel to the direction of the central applicator tube and being at the angle offset from the direction of the central applicator tube.

19. The brachytherapy applicator assembly of claim 18, wherein the plurality of needle openings are angularly spaced 5 to 45 degrees apart.

20. The brachytherapy applicator of claim 9, wherein the ring-shaped applicator has an outer diameter of 20 to 55 millimeters.

21. The brachytherapy applicator of claim 9, wherein at least one of the central applicator tube and the applicator tubes has a cross-section that is noncircular with a flattened segment.

* * * * *